US012623034B2

(12) United States Patent
Wang et al.

(10) Patent No.: US 12,623,034 B2
(45) Date of Patent: May 12, 2026

(54) SYRINGE PROTECTOR AND ITS SAFETY SYRINGE

(71) Applicant: SUZHOU SAVICRED BIOTECHNOLOGY CO., LTD., Suzhou (CN)

(72) Inventors: Jing Wang, Suzhou (CN); Hongxia Zhou, Suzhou (CN); Wei Shen, Suzhou (CN)

(73) Assignee: SUZHOU SAVICRED BIOTECHNOLOGY CO., LTD., Suzhou (CN)

( * ) Notice: Subject to any disclaimer, the term of this patent is extended or adjusted under 35 U.S.C. 154(b) by 608 days.

(21) Appl. No.: 18/025,796

(22) PCT Filed: Jun. 25, 2021

(86) PCT No.: PCT/CN2021/102380
§ 371 (c)(1),
(2) Date: Mar. 10, 2023

(87) PCT Pub. No.: WO2022/052575
PCT Pub. Date: Mar. 17, 2022

(65) Prior Publication Data
US 2023/0355893 A1 Nov. 9, 2023

(30) Foreign Application Priority Data

| | | |
|---|---|---|
| Sep. 10, 2020 | (CN) .......................... | 202010946448.8 |
| Nov. 30, 2020 | (CN) .......................... | 202022824635.7 |
| Jan. 8, 2021 | (CN) .......................... | 202120055382.3 |

(51) Int. Cl.
*A61M 5/32* (2006.01)
*A61M 5/31* (2006.01)

(52) U.S. Cl.
CPC .......... *A61M 5/326* (2013.01); *A61M 5/3137* (2013.01); *A61M 5/3245* (2013.01);
(Continued)

(58) Field of Classification Search
CPC ... A61M 5/326; A61M 5/3137; A61M 5/3245
(Continued)

(56) References Cited

U.S. PATENT DOCUMENTS

| | | | | |
|---|---|---|---|---|
| 6,613,022 B1 * | 9/2003 | Doyle | ................... | A61M 5/326 |
| | | | | 604/192 |
| 2009/0105663 A1 | 4/2009 | Brand et al. | | |

FOREIGN PATENT DOCUMENTS

| | | |
|---|---|---|
| CN | 1288391 A | 3/2001 |
| CN | 101563124 A | 10/2009 |

(Continued)

OTHER PUBLICATIONS

International Search Report of PCT/CN2021/102380.
Written Opinion of PCT/CN2021/102380.

*Primary Examiner* — Edelmira Bosques

(57) ABSTRACT

The disclosure involves a syringe protector, which is includes of an outer protection sleeve, an inner installation sleeve, and a spring; the spring is installed at the outer sleeve wall of the installed inner installation sleeve, the said spring is compressed and installed in the said outer installation sleeve, and a syringe protector is formed; the said outer installation sleeve is comprised of a inner sleeve cylinder body, and a backstop claw, a guide sliding groove, an inner stop orifice, a spring installation seat, an inner locking claw; the said inner installation sleeve is comprised of an inner cylinder body, and a backstop claw, a guide block, an outer locking claw, a claw frame, a releasing incline, a syringe (Continued)

fixing claw, and a syringe flange fixing channel. The safety syringe described in the disclosure will be installed in the above syringe protector.

21 Claims, 38 Drawing Sheets

(52) U.S. Cl.
CPC .............. *A61M 2005/3139* (2013.01); *A61M 2005/3247* (2013.01)

(58) Field of Classification Search
USPC ........................................................ 604/198
See application file for complete search history.

(56) References Cited

FOREIGN PATENT DOCUMENTS

| | | | |
|---|---|---|---|
| CN | 104411351 | A | 3/2015 |
| CN | 110970848 | A | 4/2020 |
| CN | 111888580 | A | 11/2020 |
| CN | 213609016 | U | 7/2021 |
| WO | 03097138 | A1 | 11/2003 |

* cited by examiner

SYRINGE PROTECTOR AND ITS SAFETY SYRINGE

CROSS-REFERENCE TO RELATED APPLICATIONS

This Application is a national stage application of PCT/CN2021/102380. This application claims priorities from PCT Application No. PCT/CN2021/102380, filed Jun. 25, 2021, and from the Chinese patent applications 202010946448.8 filed Sep. 10, 2020, 202022824635.7 filed Nov. 30, 2020, and 202120055382.3 filed Jan. 7, 2021, the content of which are incorporated herein in the entirety by reference.

TECHNICAL FIELD

The disclosure involves a protector for syringe, and a safety syringe including such a protector.

BACKGROUND

The disposable syringe is a most frequently used instrument in medical field, to prevent the syringe needle after use from injuring the user by accident, causing pharmaceutical contamination, or second use of the injector, after the injection is finished, the needle shall be recycled as a whole; with stricter management of the medical instrument, some authorities have required to add special protectors for the disposable syringe. After the injection is finished, the protector is activated to protect the needle to prevent needle injuring by accident, separation of the needle and injector, and improve use safety of the disposable injector.

The research on the syringe needle protector and the corresponding safety injector was carried out in the European and American countries at the earliest time, and the corresponding patented technology was mostly proposed by European and American enterprises, such as anti-stabbing safety device for syringe with Chinese patent publication No. CN104411351A, passive bolted lock ring protection device for syringe with Chinese patent publication No. CN101437561A, and disposal safety syringe with Chinese patent publication No.:CN1189222A, which are restricted by the shaping material performance and protection requirements, most of them have complicated structure and inconvenient operation, and the manufacturing costs are high.

In recent years, with domestic enterprises' emphasis on this field, related technologies emerge, such as sliding sleeve needle protector and safety syringe with Chinese patent publication No. CN203043181U, a needle protector and safety syringe with Chinese patent publication No. CN111529825A, and a syringe needle protector with Chinese patent publication No. CN105854131A; such a kind of product play a protection role for the needle, but the structure is still complicated.

To further improve operation convenience and safety of the syringe needle protector, relevant structures shall be further improved.

DESCRIPTION OF THE DISCLOSURE

The disclosure aims to provide a safety syringe to improve operation convenience and safety.

For the purpose of the above, one aspect of the disclosure offers a syringe protector, which is characterized in that, an outer protection sleeve, an inner installation sleeve, and a spring are included;

the said spring is installed at an outer wall sleeve of the said inner installation sleeve, the said spring is compressed and loaded into the outer protection sleeve, and a syringe needle protector is formed;

the said outer protection sleeve is comprised of an outer sleeve orifice, an outer sleeve tube body, a guide chute, an inner stop spigot, a spring installation seat, and an inner locking jack catch;

the said outer sleeve pipe orifice is installed at the bottom of the said outer sleeve tube body;

the said guide chute is installed on a wall surface of the said outer sleeve tube body;

the inner spigot is installed at the middle of the inner wall of the said outer sleeve tube body;

the spring installation seat is installed at the upper portion of the said outer sleeve tube body, the bottom diameter of the said spring installation seat is larger than the inner diameter of the said outer sleeve tube body, and the said spring is stored in the said spring installation seat;

an inner jack catch is installed above the said spring installation seat, and the number of the said inner locking jack catch shall be 2 and above around the circumference of the said spring installation seat;

the said inner installation sleeve is comprised of an inner sleeve body, and a backstop claw, a guide block, an outer locking block, a clamping claw frame, releasing incline, injection cam fixing claw, and injector cam fixing slot;

the said inner sleeve tube body is installed at the said outer sleeve tube body, and the said inner tube body is used to store the syringe.

the said backstop jaw is installed at the bottom of the said inner sleeve tube body, and inclines outwards; under natural status before assembling, the concentric circle diameter where the bottom of the backstop jaw is larger than the inner diameter of the said outer sleeve tube body;

the said inner sleeve tube body is installed with a guide block, which is located at the lower portion of the said inner sleeve tube body and protrudes at the outer wall surface of the said inner sleeve tube body; and the said guide block is clipped into the said guide chute;

the top of the said inner sleeve tube body is installed with a locking mechanism of the protector, a releasing mechanism of the protector, and fixer of the syringe;

the said protection device locking mechanism is comprised of an outer locking jack catch, which is fastened with the said inner locking jack catch to lock the syringe needle protector; and the said outer locking jack catch suspension arm is fixed on the said jack catch frame;

the said protector releasing mechanism is comprised of a releasing slope, which is installed at the inside of the suspension arm above the said outer locking jack catch and below the said jack catch frame;

the said syringe fixing mechanism is comprised of a syringe cam fixing jaw and a syringe cam fixing groove, the later of which is located at the top of the said inner sleeve tube body, multiple syringe cam fixing jaws are installed above the syringe cam fixing groove, and a guide slope is installed at the said syringe cam fixing jaw.

As further improvement of the disclosure, the said outer protection sleeve is installed with a locking protection piece, which is installed at the outside of the said inner locking jack catch; the insertion space of the said outer locking jack catch is reserved between the said inner locking jack catch and the said locking protection piece.

As further improvement of the disclosure, a handle rib is installed on the said outer protection sleeve, and 2 pieces of the said handle ribs are installed and are installed on the said spring installation seat or the outer wall of the said outer sleeve tube body.

Further, a bottom of the said handle panel is installed with multiple anti-slipping strips.

As a further improvement of the disclosure, the said outer sleeve orifice inclines towards inside and forms an inner cone.

As a further improvement of the disclosure, minimum 2 said guide chutes are installed and are arranged on the wall of the said outer protection sleeve symmetrically; minimum 2 guide blocks are installed and are arranged on the wall surface of the said inner sleeve cylinder body.

As a further improvement of the disclosure, multiple spring limit clips are installed at the inside of the bottom of the said spring installation seat, the said spring limit clips project out and are scattered at the top of the said outer sleeve tube body; the inner diameter of the said spring is clipped into the outside of the limit position of the convex structure of the said limit clips.

As a further improvement of the disclosure, a needle sleeve backstop piece is arranged at the bottom of the said inner sleeve tube body, and the said needle sleeve backstop piece inclines inwards; the concentric circle where the bottom of the needle sleeve backstop piece is less than the inner diameter of the said inner sleeve tube body;

When the needle sleeve of the syringe is not loaded, the concentric circle diameter where the bottom of the needle sleeve backstop piece is located is less than the top outer diameter of the syringe needle sleeve.

Further, the said needle sleeve backstop piece and the said backstop jaw shall be minimum 2; and the said needle sleeve backstop piece and the said backstop jaw interval shall be scattered on the bottom of the said inner sleeve tube body homogeneously.

As a further improvement of the disclosure, the bottom of the said guide block is communicated with the said inner sleeve tube body via a tie bar, the upper portion of the said guide block is suspended in air, and the said guide block inclines inwards along the said tie bar.

Further, the said inner sleeve tube body where the said guide block is located is installed with a window, whose direction is corresponding to the direction of the guide chute.

As a further improvement of the disclosure, a fixed step for piston is installed at the lower portion of the releasing slope, and the said fixing step for piston is located at inside the suspension arm above the said outer locking arm; the said fixing step for piston is higher than the top of the fixing jaw of the said syringe cam.

As a further improvement of the disclosure, the said outer protection sleeve and the said inner installation sleeve are installed with an inner locking catch jack and an outer locking catch jack for the left and right limit structure and form a safety snap joint, including the inner locking catch jack and an outer locking catch jack; under natural status, the said outer locking catch jack fastens the said inner locking catch jack; the contact between catch jack body of the said inner locking catch jack and the said outer locking catch jack is installed with the left and right limit structure.

Further, the said left and right limit structure is that, both sides of the said outer locking jack catch are installed with an inner catch jack limit body, both sides of which form an inner jack catch storage groove; under locking status, the said inner locking jack catch is located within the said inner jack catch storage groove; the said inner jack catch limit body limits the leftward and rightward directions of the inner locking jack catch.

Further, the said left and right limit structure is that, the said inner locking catch jack is installed with an inner jack catch fastened with the said outer locking catch jack; both sides of the said inner jack catch are installed with an outer jack limit body; under locking status, a jack catch surface of the said outer locking jack catch is clipped between the outer catch jack limit body on both sides and shall be fastened with the inner catch jack surface; the said outer jack catch limit body limits the said outer locking catch jack at the left and right directions.

Further, the said and left and right limit structure is that, a groove is made in the middle of the jack catch of the said outer locking catch jack to form an inner jack catch storage groove, and both sides of the jack catch body of the said locking outer jack catch form a limit body for the inner jack catch;

a convex inner catch jack convex block is installed at the lower portion of the middle of the catch jack body of the said inner locking jack catch; the width of the said inner catch jack convex block matches the width of the said inner catch jack storage groove;

under locking status, the said inner locking jack catch contacts the said outer locking jack catch, and the said inner jack catch clips into the said inner jack catch storage groove.

Further, the center of the body of the said released slope is installed with a concave slot communicated with the said inner jack catch storage channel.

Further, the said left and right limit structures are, the middle of the said inner locking jack catch is installed with a concave groove to shape a storage groove of the outer jack catch, and the lower portion of the middle of the said outer locking jack catch is installed with an outer jack catch convex block; and width of the said outer jack catch convex block matches the width of the said outer jack catch storage groove;

under locking status, the said inner locking jack catch contacts the said outer locking jack catch, and the said outer jack catch convex block clips into the said outer jack catch storage groove.

Under locking status, the said inner locking jack catch contacts the said outer locking jack catch, and the said outer jack catch is clipped into the said storage channel of the said outer jack catch.

Further, an outer jack catch guide slope is installed at the bottom of the said outer locking jack catch.

Further, the top of the said inner locking jack catch is installed with a guide slope.

As further improvement of the disclosure, the outer surface of the outer sleeve cylinder of the said outer protection sleeve is free of convex structure;

an inner concave orifice is installed at the middle of the inner wall surface of the outer sleeve tube body of the said outer protection sleeve;

the bottom of the inner installation sleeve is installed with a backstop claw;

the said backstop jaw is sprung up after the said inner installation sleeve and the said outer protection sleeve have been triggered and clipped above the said inner spigot.

Further, an inner guide chute is installed at the inner wall surface of the outer sleeve tube body of the said outer protection sleeve, and the said inner spigot is located at the said inner guide chute.

Still further, when the said backstop jaw is locked with the said outer installation sleeve in the said inner installation sleeve, it is locked in the said inner guide chute.

Further, the said outer protection sleeve is installed with a guide chute;

the bottom of the said inner installation sleeve is installed with a guide block;

the said guide block is clipped into the said guide chute.

Still further, the said guide chute is through the wall surface of the said outer sleeve tube body.

Even still further, after the said guide block is clipped into the said guide block, the outside of the said guide block is lower than the outer surface of the said outer sleeve tube body.

Further, the said guide chute is not communicated with the wall surface of the said outer sleeve tube body; the outer surface of the outer sleeve tube body of the said outer protection sleeve is continuous cylindrical surface.

The $2^{nd}$ aspect of the disclosure offers a safe syringe, including a syringe;

it is characterized in that the syringe is installed at the inner installation sleeve of the said syringe protector.

The syringe protector of the disclosure aims to protect the syringe needle and is installed at the syringe in advance to shape a safety syringe and is to be activated with medicine pushed in the syringe; the syringe protector is installed with 2 statuses, which are locking status and protection status after releasing; under the locking status, the said inner locking jack catch and the said outer locking jack catch are fastened and locked to compress the spring and store energy; in the process of use, the syringe is installed in the said inner installation sleeve of the said syringe protector, the said syringe cam is clipped into the said cam fixing groove, whose fixing jaw is used for locking; then, remove the needle sleeve to expose the needle for injection; in the process of injection, push the piston rod and push the medicine; at the final stage of pushing medicine, the piston rod struts the said outer locking jack catch and separate the said inner locking jack catch, and the snap joint is released, activated and fixed in the step to lock the piston position rod; after medicine pushing is finished, the operator releases the syringe and the syringe protector to start the spring, the said outer protection sleeve and the said installation sleeve move to make the said outer sleeve pipe orifice cover and protect the needle; at this moment, the said guide block slides to the top of the guide groove to prevent separation between the said outer protection sleeve and the said inner protection sleeve; meanwhile, the said backstop jaw flicks and clips into the said inner stop orifice to prevent re-contracting the said outer protection sleeve and the said installation sleeve and exposing the needle.

The syringe protector of the disclosure is comprised of the said outer protection sleeve and the said inner installation sleeve with plastics, in particular to related components of the said inner installation sleeve, such as the said needle sleeve backstop piece, backstop jaw, connecting bar, outer locking jack catch and syringe cam fixing jaw of excellent resilience, and shall be wrapped and elastically reset based on requirements in different stages.

The syringe protector of the disclosure is made of an outer protection sleeve and an inner installation sleeve made of plastics, and the materials are of certain elasticity and flexibility and can be easily assembled.

The syringe protector of the disclosure, compared with the existing protector, is featured with simple structure, and easy production and assembling, and protecting the syringe injector effectively; meanwhile, after the injection is finished, the piston rod of the syringe is locked to avoid a second use.

Under locking status of the safety snap joint of the disclosure, the said inner locking jack catch contacts the said outer locking jack catch, the special parts are combined, the left and right limit bodies are installed on both sides to ensure that the said outer protection sleeve and the said inner protection sleeve will not deflect by external stress, and the said inner locking jack catch and the said outer jack catch are separated to result in activation in error.

When the safety snap joint of the disclosure is activated and released, the medicine is pushed by the piston rod to release and activate the piece to approach the said outer locking jack catch, finally, the said releasing snap joint contacts the said releasing slope, and moves downwards the said releasing slope to push the said outer locking jack catch, the said outer locking jack catch rotates towards the connection along the jack catch frame to separate the left and right limit body, and the said outer locking jack catch is thoroughly separated from the said outer locking jack catch; finally, the operate releases the hands, the spring acts, and pushes the said outer protection sleeve to be far away from the said inner installation sleeve to activate the syringe protector.

Based on the existing jack catch structure, the left and right limit structures are arranged for the safety snap joint of the disclosure for limiting the left and right directions to improve storage and transporting safety under locking status after finishing assembling of the syringe protector and avoid error triggering.

The syringe protector of the disclosure is to improve related structure of the inner stop orifice of outer sleeve tube body of the protective outer sleeve to receive a complete outer surface for sticking labels or etching pictures or texts.

The safety syringe of the disclosure is that the syringe is installed in the syringe protector of the disclosure.

The disclosure structure is simple and can be easily realized, which meets customers' sticking labels on the external surface, or etching pictures and texts.

Figure 1:
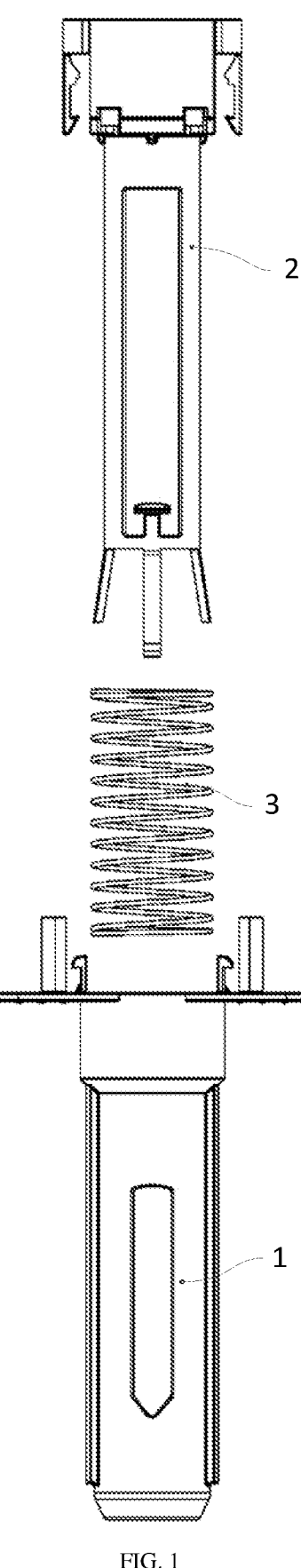
FIG. 1 is part explosive view of protector of the disclosure.

Marks of attached Figures: outer protection sleeve 1, inner installation sleeve 2, and spring 3; syringe tube 4, piston rod 5, needle 6, and needle sleeve 7;

Outer sleeve pipe orifice 11, outer sleeve tube body 12, guide chute 13, inner stop orifice 14, spring installation seat 15, inner locking catch jack 16, locking protection piece 17, handling rib 18; spring limit clip 151; anti-stripping bar 19; inner guide groove 141;

Inner jack catch surface 117, outer jack catch limit body 118; inner jack catch convex block 119;

Needle sleeve backstop piece 21, backstop jaw 22, guide block 23, outer locking jack catch 24, jack catch frame 25, releasing slope 26, piston fixing step 27, syringe cam fixing jaw 28, syringe cam fixing groove 29; connecting bar 231;

Inner jack catch limit body 227, and inner jack catch storage groove 228;

Syringe cam 41; releasing activation piece 51, pushing head 52.

Embodiment

The disclosure is further described combined with the following attached figures and embodiments.

As shown in FIG. 1, the syringe protector of the disclosure is comprised of an outer protection sleeve 1, an inner installation sleeve 2, and a spring 3; the said spring 3 is installed at the said inner installation sleeve 2, and compressed and installed into the said outer installation sleeve, namely the syringe protector of the disclosure is formed and is used after assembling.

Figure 2:
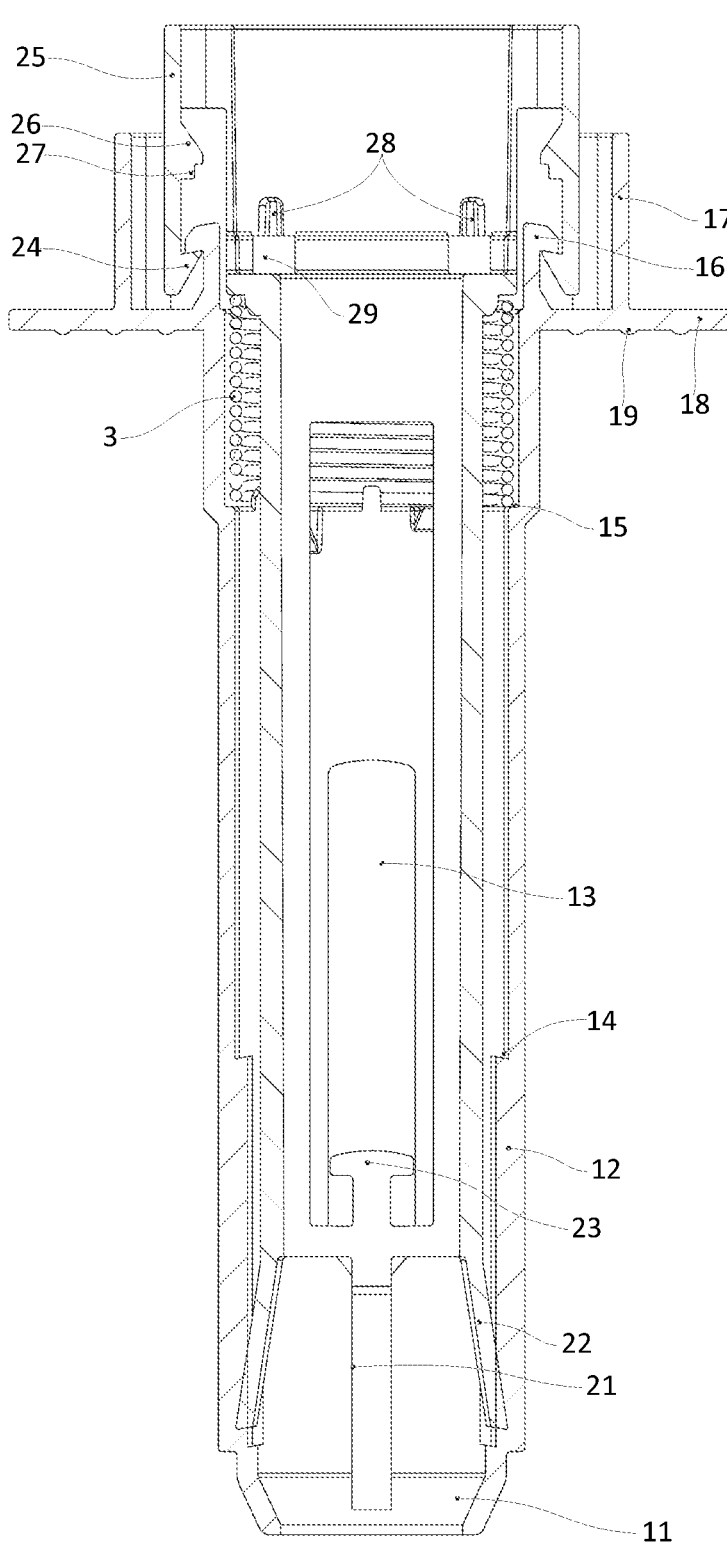
FIG. 2 is assembling section view of protector of the disclosure.
Figure 3:
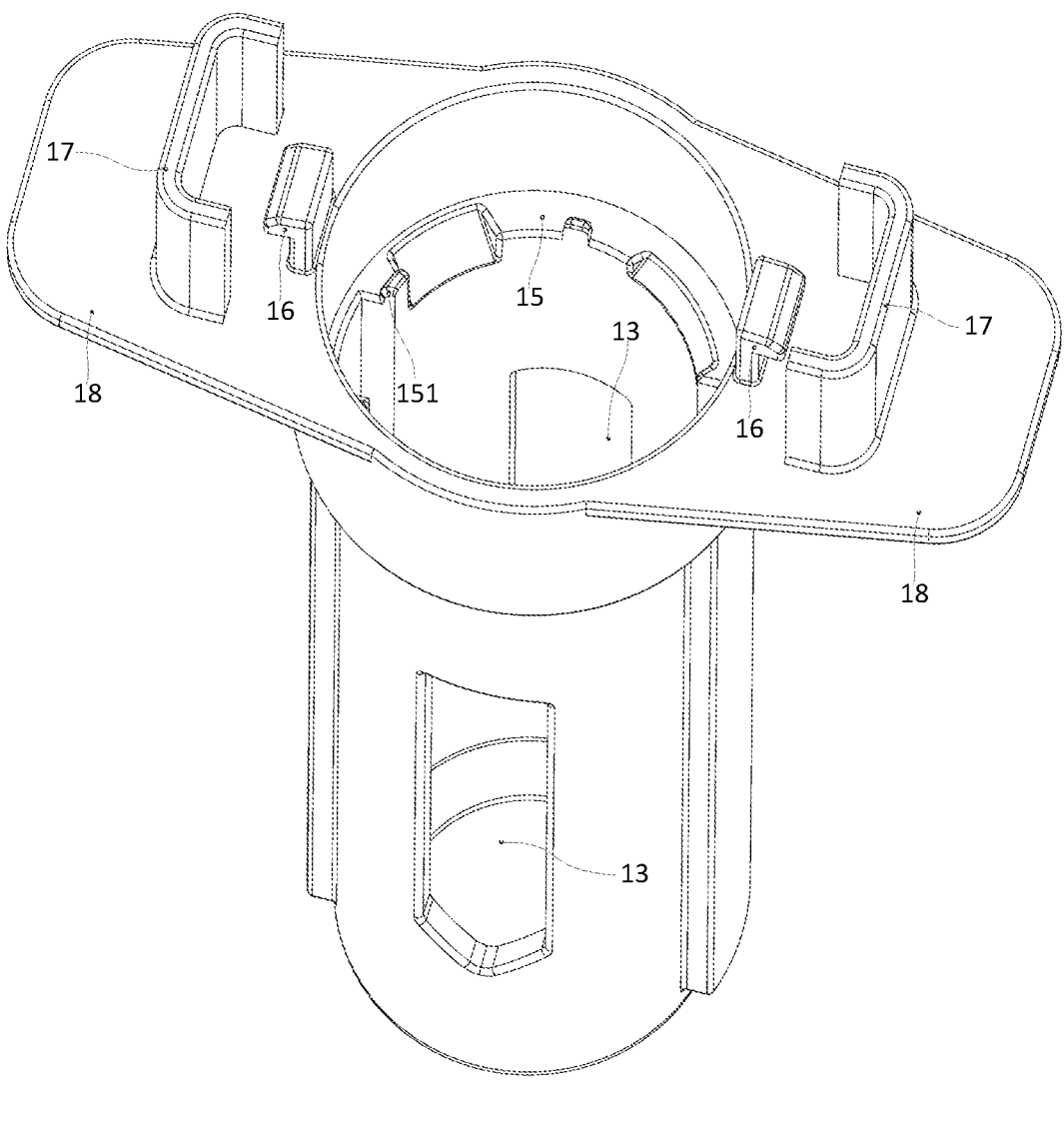
FIG. 3 is schematic diagram of structure of the outer protection sleeves of the disclosure.

As shown in FIG. 2 and FIG. 3, the said outer protection sleeve 1 is comprised of an outer protection sleeve 11, an outer sleeve tube body 12, a guide chute 13, an inner stop orifice 14, a spring installation seat 15, an inner locking jack catch 16, a locking protection piece 17, and a handle rib 18; the orifice of the outer sleeve pipe orifice 11 inclines inwards to shape an internal cone and play a role of protection; the said outer sleeve pipe orifice 11 is arranged at the bottom of the said outer sleeve tube body; the wall surface of the said outer sleeve tube body 12 is arranged with a guide groove 13, 2 of which are arranged preferably and symmetrically; an inner stop orifice 14 is arranged in the middle of the inner wall of the said outer sleeve tube body 12, and 2 inner stop orifices 14 are arranged preferably and symmetrically; the upper portion of the said outer sleeve tube body is installed with a spring installation seat, the bottom diameter of the said spring installation seat is larger than the inner diameter of the said outer sleeve tube body 12, the said spring installation seat 15 stores the spring 3, whose diameter matches the diameter of the said spring installation seat, and the said spring 3 will not be clipped into the said outer sleeve tube body 12; preferably, multiple spring limit clips 151 are installed inside the bottom of the said spring installation seat and limit inside the bottom of the said spring 3 to prevent the spring 3 from entering the said outer sleeve tube body 12 by mistake; an inner locking jack catch 16 is installed above the said spring installation seat 15 and shall be arranged in minimum 2 around the peripheral of the said spring installation seat 15; a handle rib 18 is installed, regularly, two pieces of the said handle rib 18 shall be in pair, which are arranged on the outer wall of the said spring installation seat 15 or the said outer sleeve tube body 12 for operators' hand operation; multiple anti-stripping bars 19 are arranged at the bottom of the said handle ribs 18 to increase friction; preferably, outside of the said inner locking jack catch 16 is installed with the corresponding locking protection piece 17, which is arranged on the upper surface of the said handle rib 18, and a locking installation space between the said inner locking jack catch and the said locking protection piece is reserved.

Figure 4:
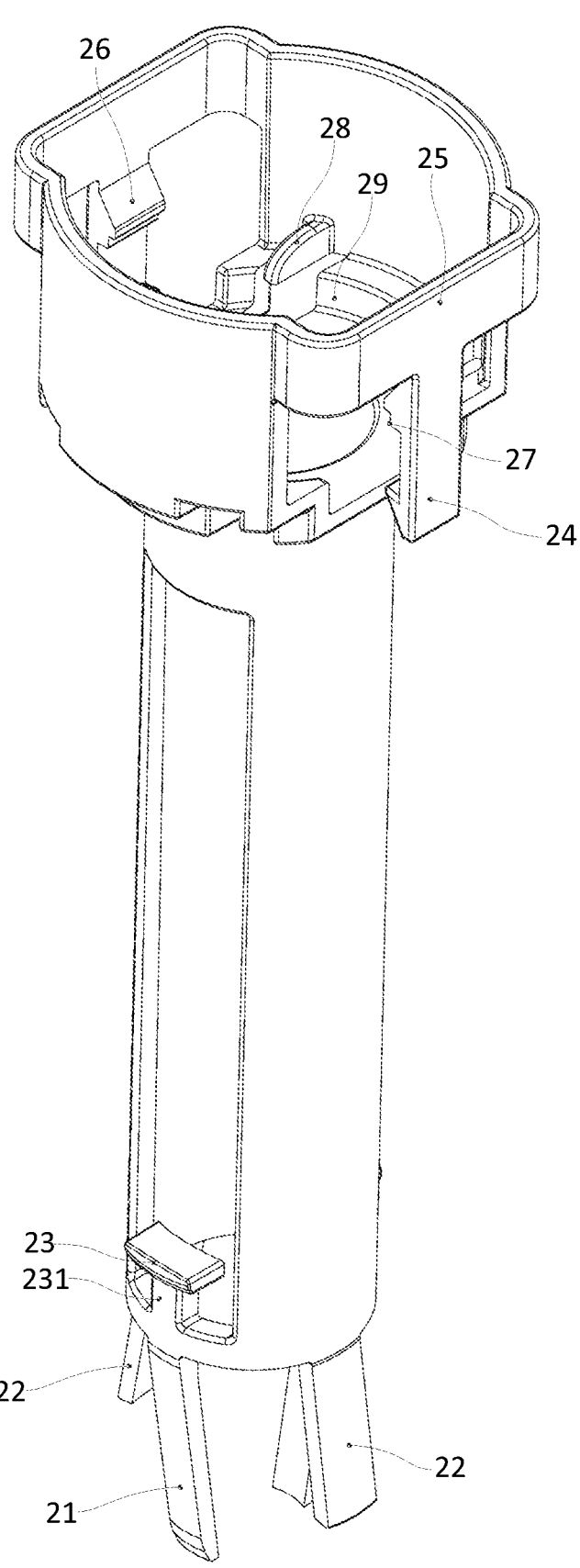
FIG. 4 is structure schematic diagram 1 of the inner installation sleeve of the disclosure.
Figure 5:
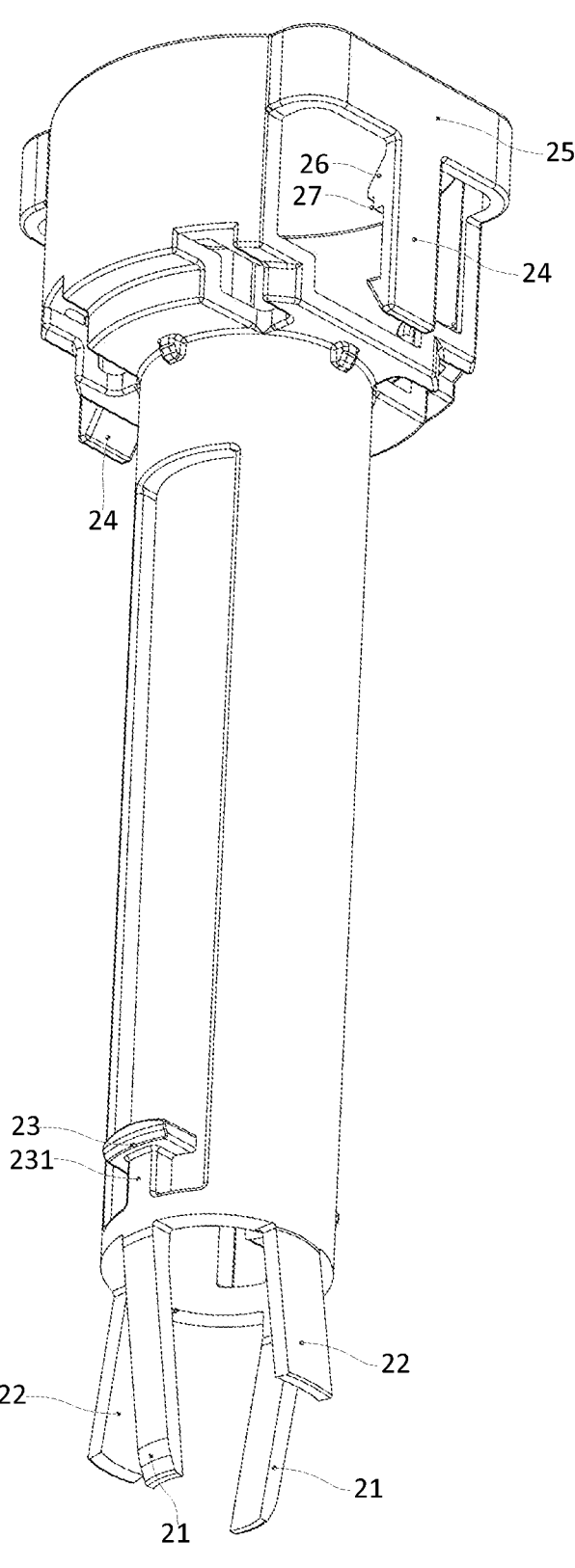
FIG. 5 is structure schematic diagram 2 of the inner installation sleeve of the disclosure.

As shown in FIG. 2, FIG. 4, and FIG. 5, the said inner installation sleeve 2 is comprised of an inner sleeve tube body, a needle sleeve backstop piece 21, a backstop jaw 22, a guide block 23 an outer locking jack catch 24, a jack catch frame 25, a releasing slope 26, a piston fixing step 27, a syringe cam fixing jaw 28, and a syringe cam fixing chute; in the process of assembling, the said inner sleeve tube body is installed within the said outer sleeve tube body 12, which is used to contain the syringe; the bottom of the said inner sleeve tube body is installed with a needle sleeve backstop piece 21 and a backstop jaw 22; the said needle sleeve backstop piece 21 inclines inwards, and the backstop jaw 22 inclines outwards; preferred, the said needle sleep backstop piece 21 and the said backstop jaw 22 shall be minimum 2, the embodiment shall be minimum 2 symmetrically with interval of 90°, which are installed at the bottom of the said inner sleeve tube body; under natural status, the bottom diameter comprised of multiple said needle sleeve backstop pieces is less than the inner diameter of the said inner sleeve tube body, and the bottom diameter comprised of the said multiple backstop jaws 22 is larger than the inner diameter of the said outer sleeve cylinder body; the said inner cylinder is installed with a guide block 23, which is located at the lower portion of the said inner sleeve tube body and projects over the outer wall surface of the said inner tube sleeve body; the said guide block 23 is clipped into the said guide groove 13; preferably, the bottom of the said guide block 23 is communicated with the said inner sleeve tube body through the connecting bar 231, the upper portion of the said guide block is suspended in air, in the process of assembling, the said guide block 23 is extruded by the inner wall of the said outer sleeve tube body and inclines inwards along the said connecting bar 231 and slides into the said guide groove 13 for easy assembling. Preferably, a window is arranged at the said inner sleeve tube body where the guide block is located, corresponding to the said guide groove, which is easy to check the medicine status within the syringe.

The top of the said inner installation sleeve is installed with the protector locking mechanism, the protector releasing mechanism, and the syringe fixing mechanism.

The locking mechanism of the said protector is comprised of an outer locking jack catch 24, which is interfaced with the said inner locking jack catch to lock the protector; a suspension arm of the said outer locking jack catch 24 is fixed on the said jack catch frame 25. When the said inner installation sleeve 2 presses down into the said outer protection sleeve 1, the bottom of the said outer locking jack catch 24 contacts the top of the said inner locking jack catch 16. After continuing pressing down, the said outer locking jack catch 24 rotates around the said jack catch frame 25, both jack catches are mutually fastened, and the spring 3 is compressed to finish assembling of the syringe protector.

The said protector releasing mechanism is comprised of a releasing slope 26, which is arranged inside the suspension arm above the said outer locking jack catch 24 and below the said jack catch 25.

The said syringe fixing mechanism is comprised of a syringe cam fixing jaw 28, a syringe cam fixing groove 29, the later of which is installed at the top of the said inner sleeve cylinder, multiple said syringe cam fixing jaws 28 are located above the said syringe cam fixing groove 29, and a guide slope is installed at the said syringe cam fixing jaw 28.

Further, a piston fixing step 27 is installed below the said releasing slope 26 and is located inside the suspension arm above the said outer locking jack catch 24; the said piston fixing step 27 is higher than the top of the said syringe cam fixing jaw 28.

Figure 6:
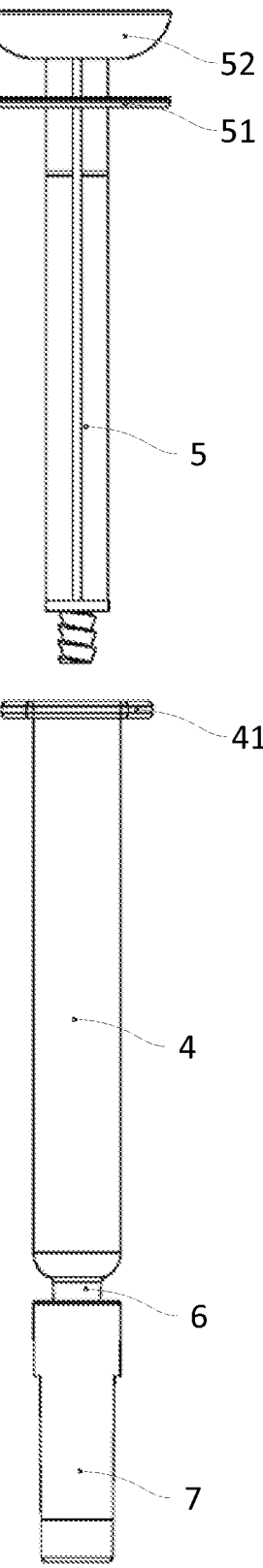
FIG. 6 is explosive view of part of the syringe of the disclosure.

As shown in FIG. 6, the syringe is comprised of a syringe tube 4, a piston rod 5, a needle 6, and a needle sleeve 7; the top of the said syringe tube 4 is installed a syringe cam 41; a pushing head 52 is installed at the top of the said piston rod 5; further, the releasing and activation piece 51 is installed below the said pushing head 52; under some situations, the said pushing head 52 shall be flattened to realize the functions of the releasing and activation piece 51.

Figure 7:
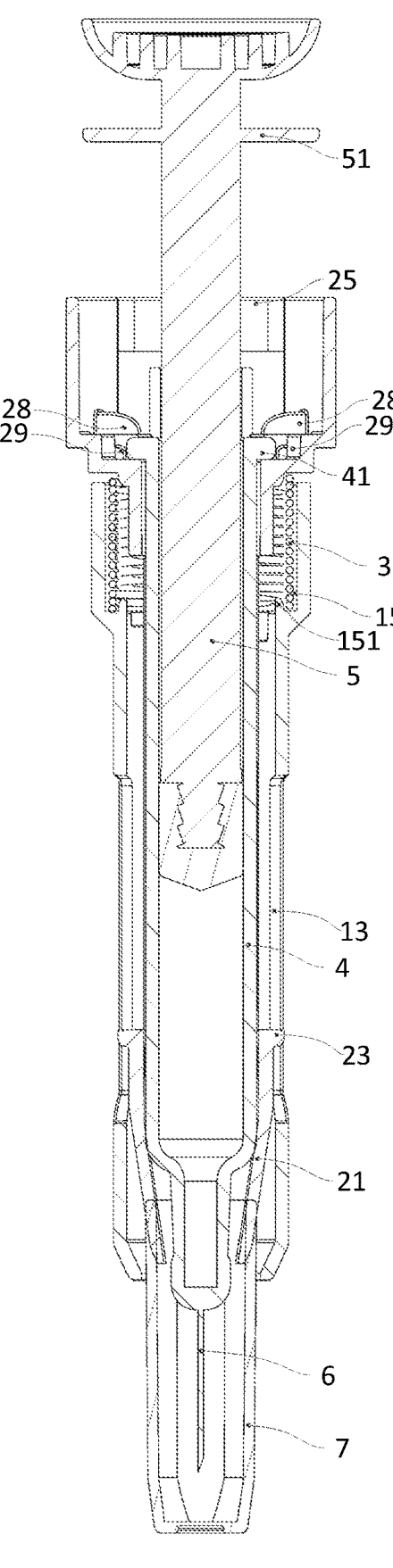
FIG. 7 is assembling section view of the safety syringe of the disclosure.
Figure 8:
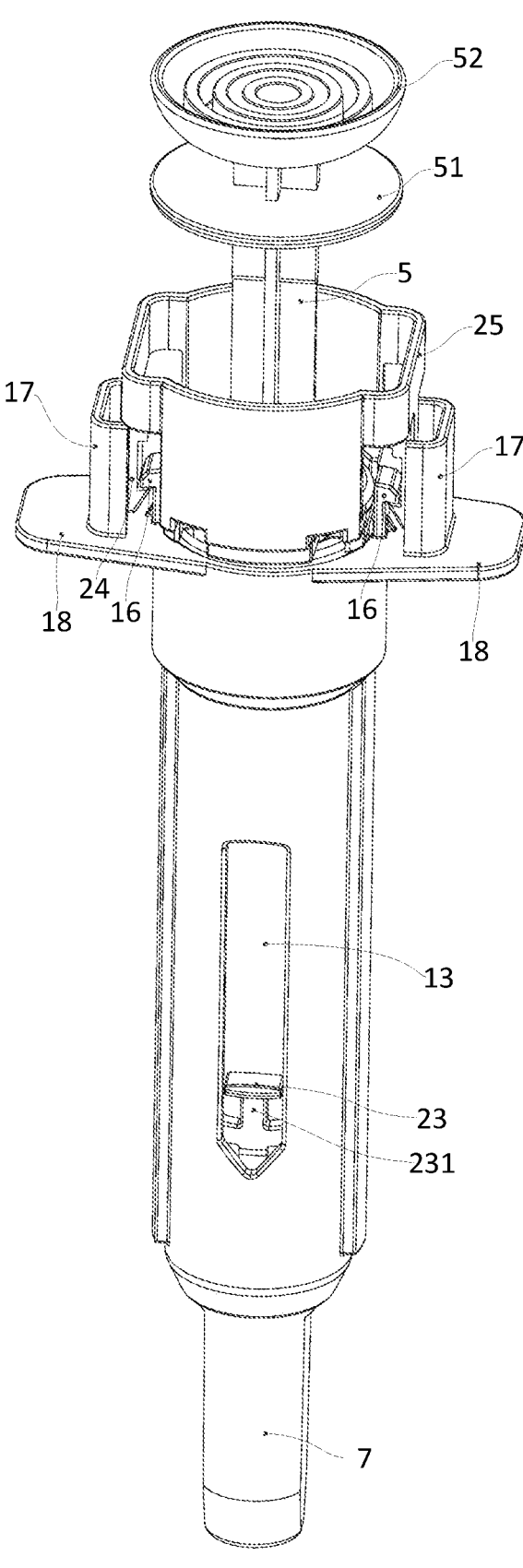
FIG. 8 is assembling structure schematic diagram 1 of the safety syringe of the disclosure.

As shown in FIG. 7 and FIG. 8, after the syringe is pre-filled with medicine in advance, it is installed in the said inner sleeve tube body of the said inner installation sleeve, the said syringe cam 41 of the said syringe tube 4 extrudes the upper slope of the said syringe fixing jaw 28, which is bent and deformed along the root of the said syringe cam fixing jaw 28 and is pressed into the fixing groove of the said syringe cam fixing groove, the said syringe cam fixing jaw 28 is elastically reset to reset the syringe cam 41 to make the syringe fixed within the said syringe protector.

Figure 9:
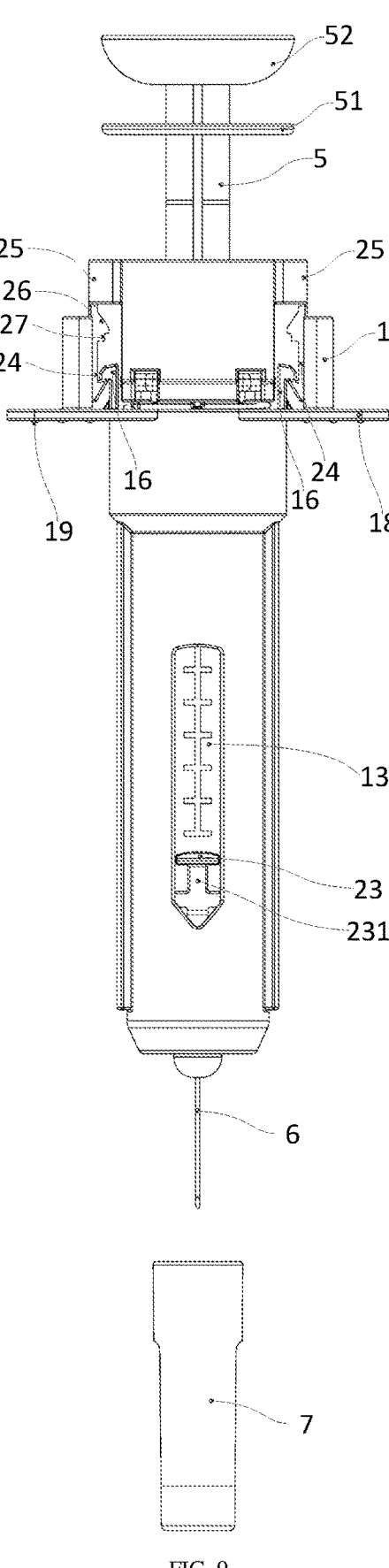
FIG. 9 is assembling structure schematic diagram 2 of the safety syringe of the disclosure.

As shown in FIG. 9, in the process of use, remove the needle sleeve 7 and expose the needle 6; at this moment, the said needle sleeve backstop piece 21 is reset elastically to prevent the needle sleeve 7 from re-inserting again and a second use; hold the handle rib 18, push the said pushing head 52, and the needle 6 is used for medicine injection.

Figure 10:
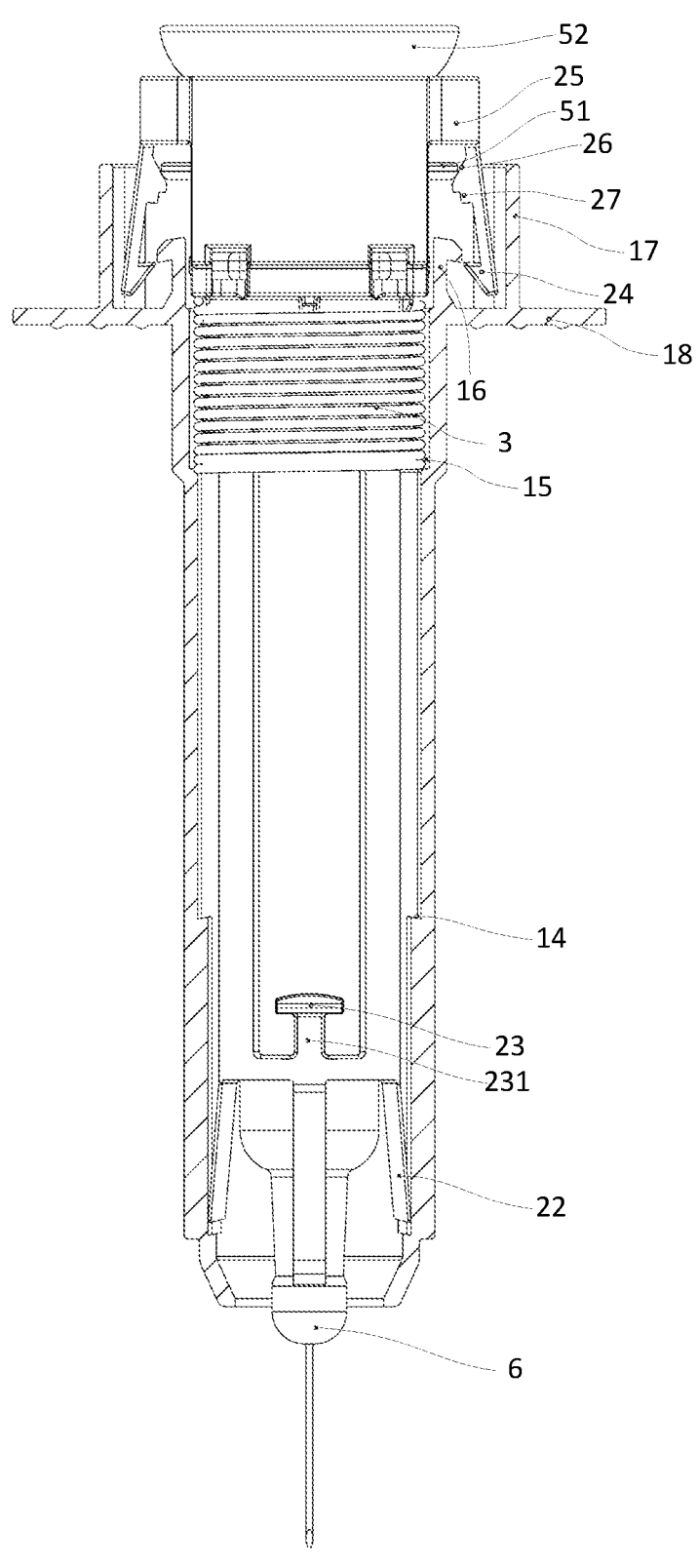
FIG. 10 is the section view 1 of the protection releasing process of the safety syringe of the disclosure.
Figure 11:
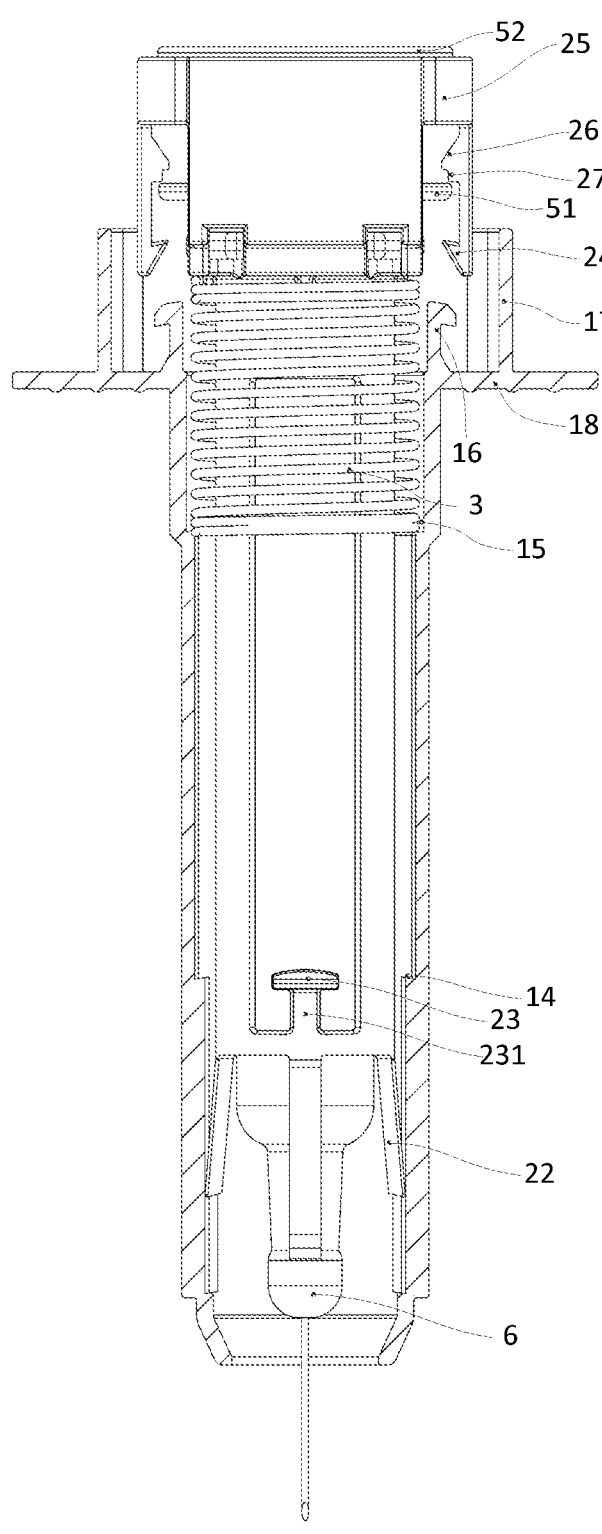
FIG. 11 is section view 2 of the protection releasing process of the safety syringe of the disclosure.

As shown in FIG. 10 and FIG. 11, at the final stage of medicine injection, the said releasing and activation piece 51 is clipped into the releasing slope 26, the outer locking jack catch 24 is opened to separate from the inner locking jack catch 16, finally, the said releasing and activation piece 51 is completely clipped into the said piston fixing step 27 to finish the activation releasing and start releasing.

Figure 12:
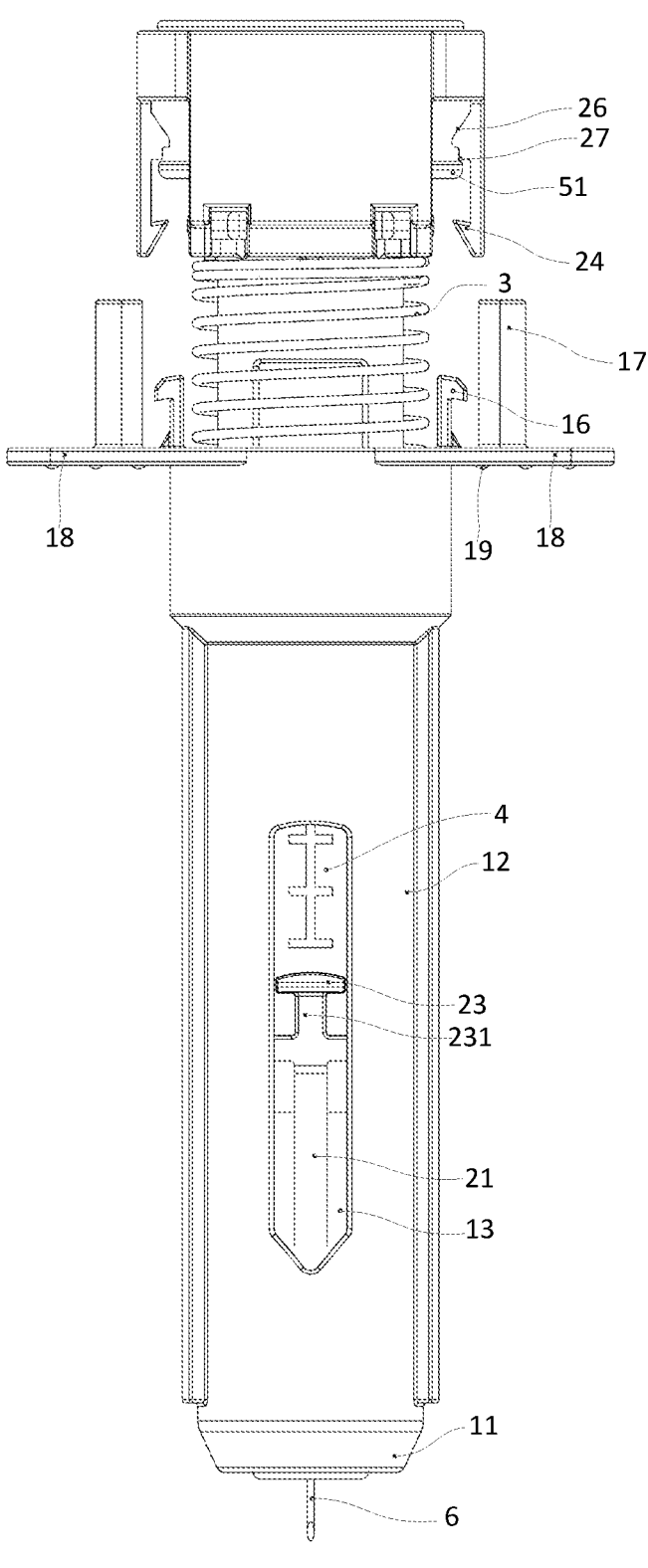
FIG. 12 is schematic diagram of the protection releasing process of the safety syringe of the disclosure.

As shown in FIG. 12, after the injection has been finished, the said releasing and activation piece 51 has been completely clipped into the said piston fixing step 27, and the said piston rod 5 and the said syringe tube 4 are fixed; the operator releases the intrinsic safety syringe, the spring 3 starts releasing, the said outer protection sleeve 1 and the said inner installation sleeve 2 start relative movement, the said inner locking jack catch 16 and the said outer locking catch jack 24 are separated, and the said outer sleeve pipe orifice shields and protects the needle 6; in the process, the said guide block 23 slides towards the said chute 13.

Figure 13:
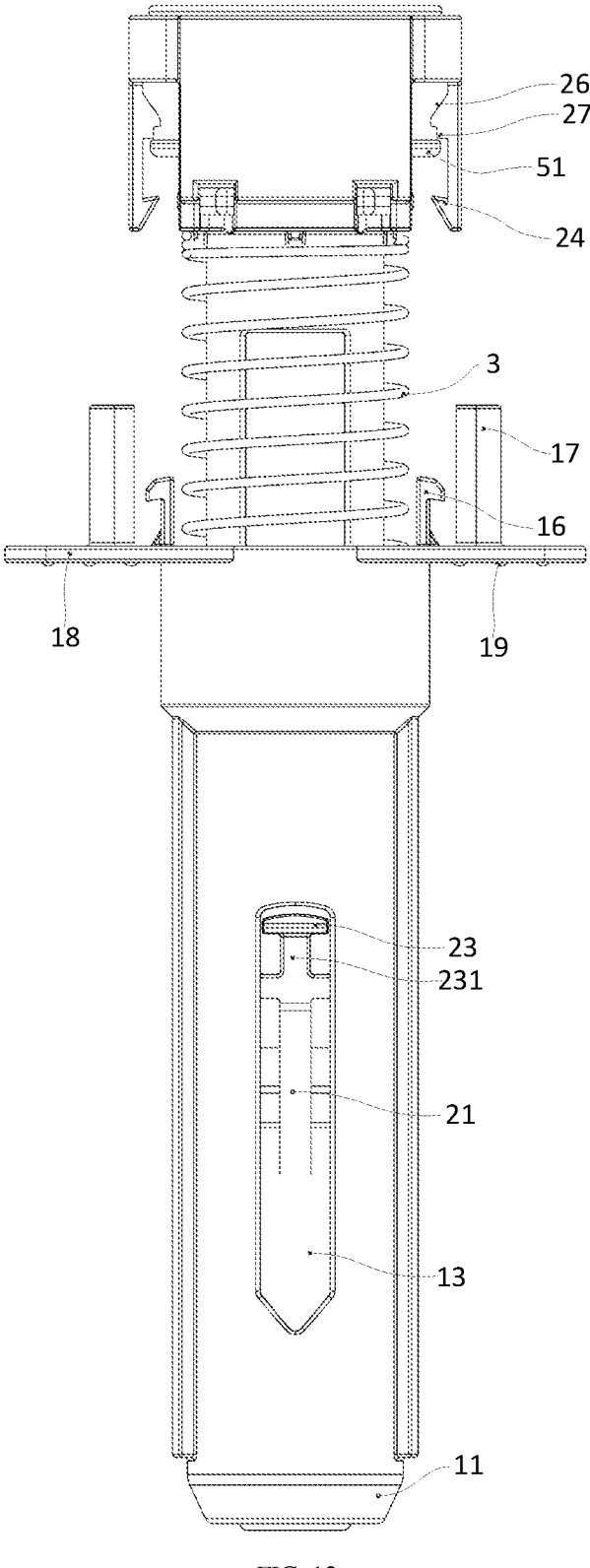
FIG. 13 is schematic diagram of the protection status of the safety syringe of the disclosure.
Figure 14:
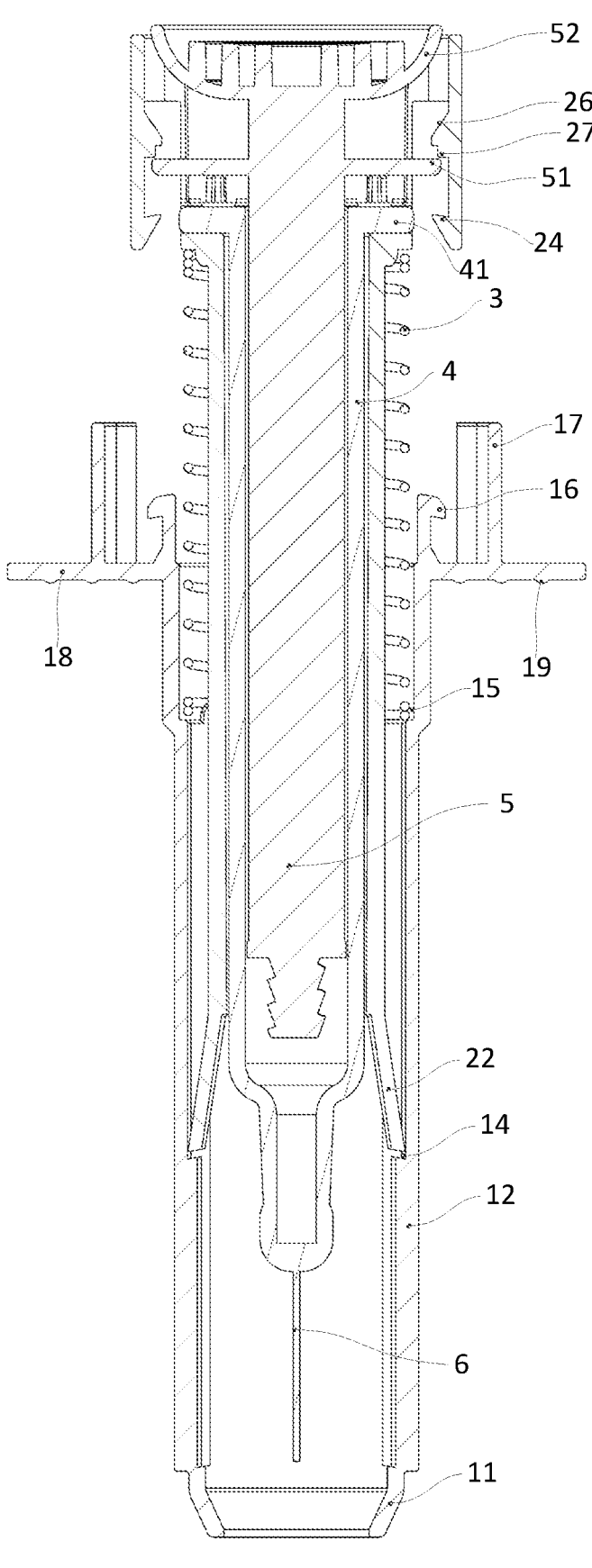
FIG. 14 is section view 1 of protection status of safety syringe of the disclosure.
Figure 15:
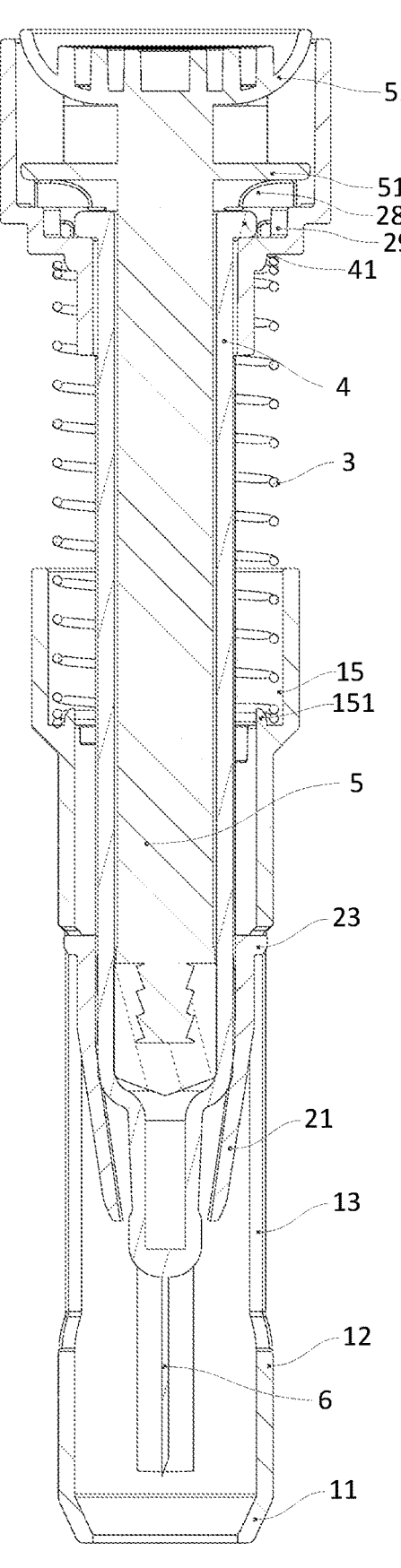
FIG. 15 is section view 2 of protection status of safety syringe of the disclosure.
Figure 16:
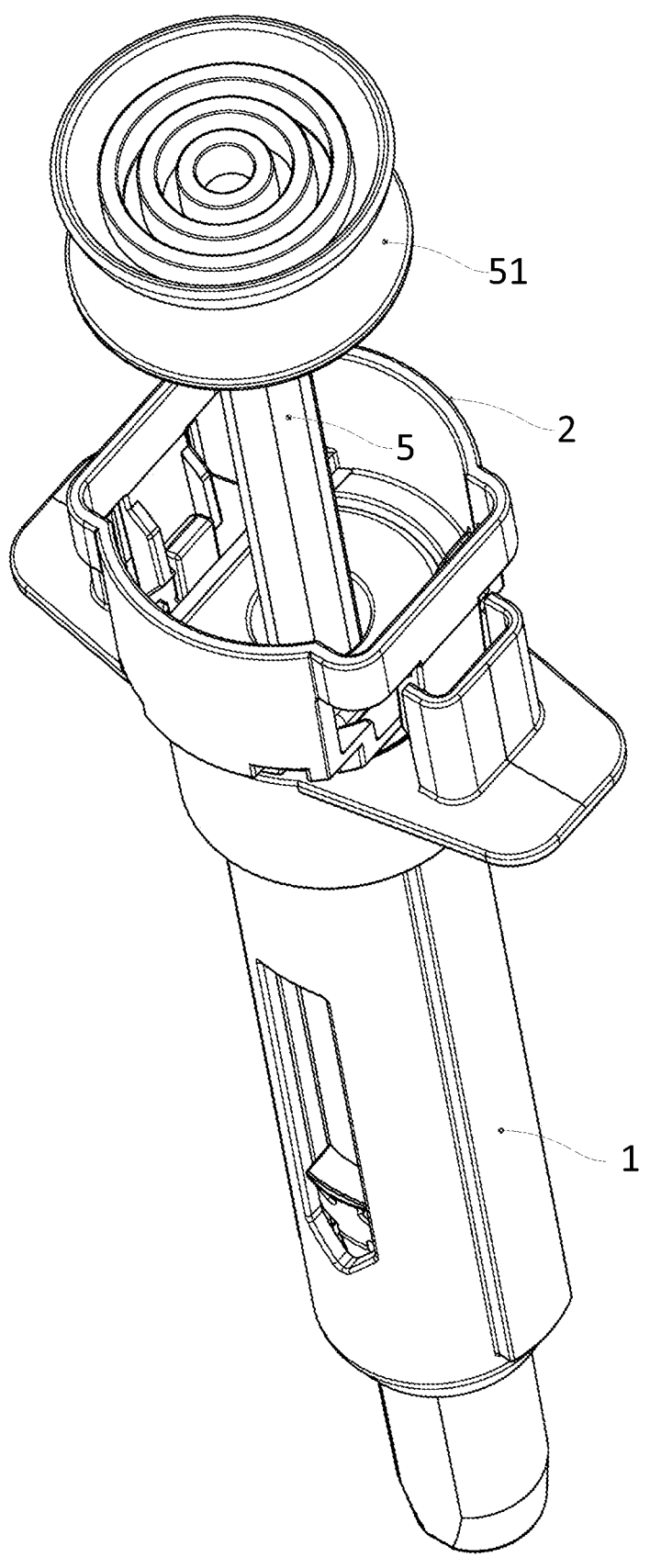
FIG. 16 is schematic diagram of overall structure of the protector of embodiment 1 of safety snap joint of the disclosure.
Figure 17:
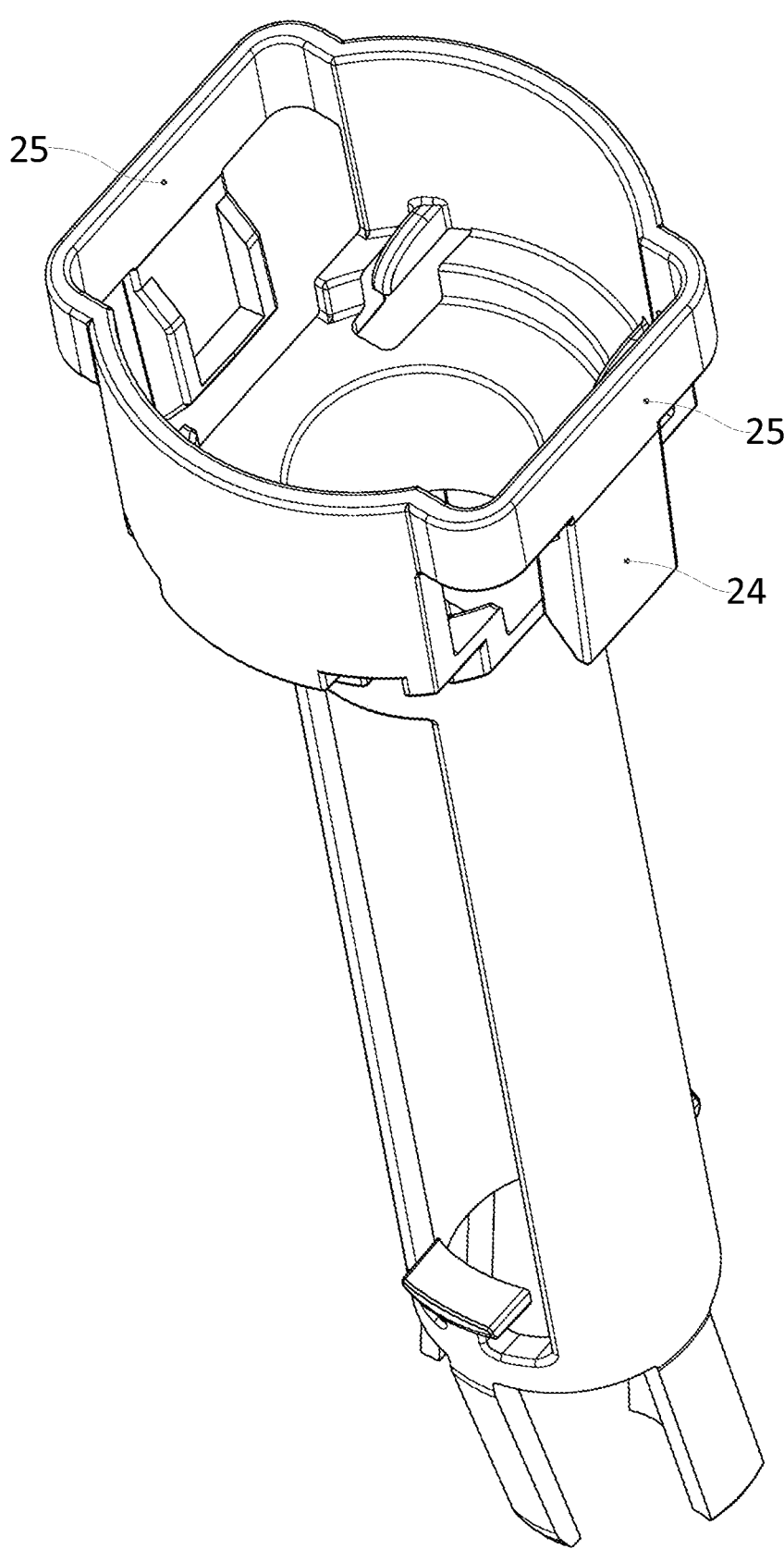
FIG. 17 is schematic diagram of overall structure of the inner installation sleeve of embodiment 1 of snap joint of the disclosure.
Figure 18:
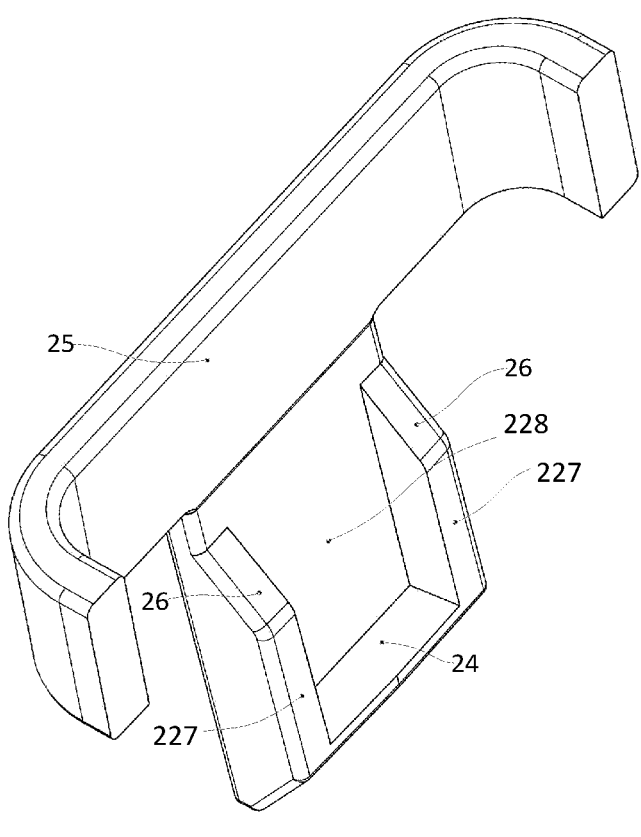
FIG. 18 is schematic diagram 1 of overall structure of the outer locking jack catch of embodiment 1 of the safety snap joint of the disclosure.
Figure 19:
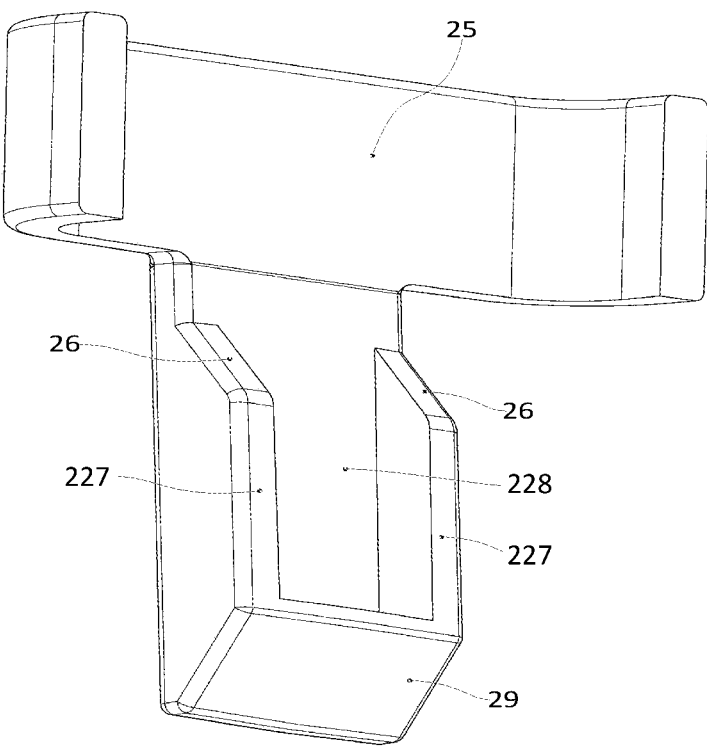
FIG. 19 is schematic diagram 2 of overall structure of the outer locking jack catch of embodiment 1 of the safety snap joint of the disclosure.
Figure 20:
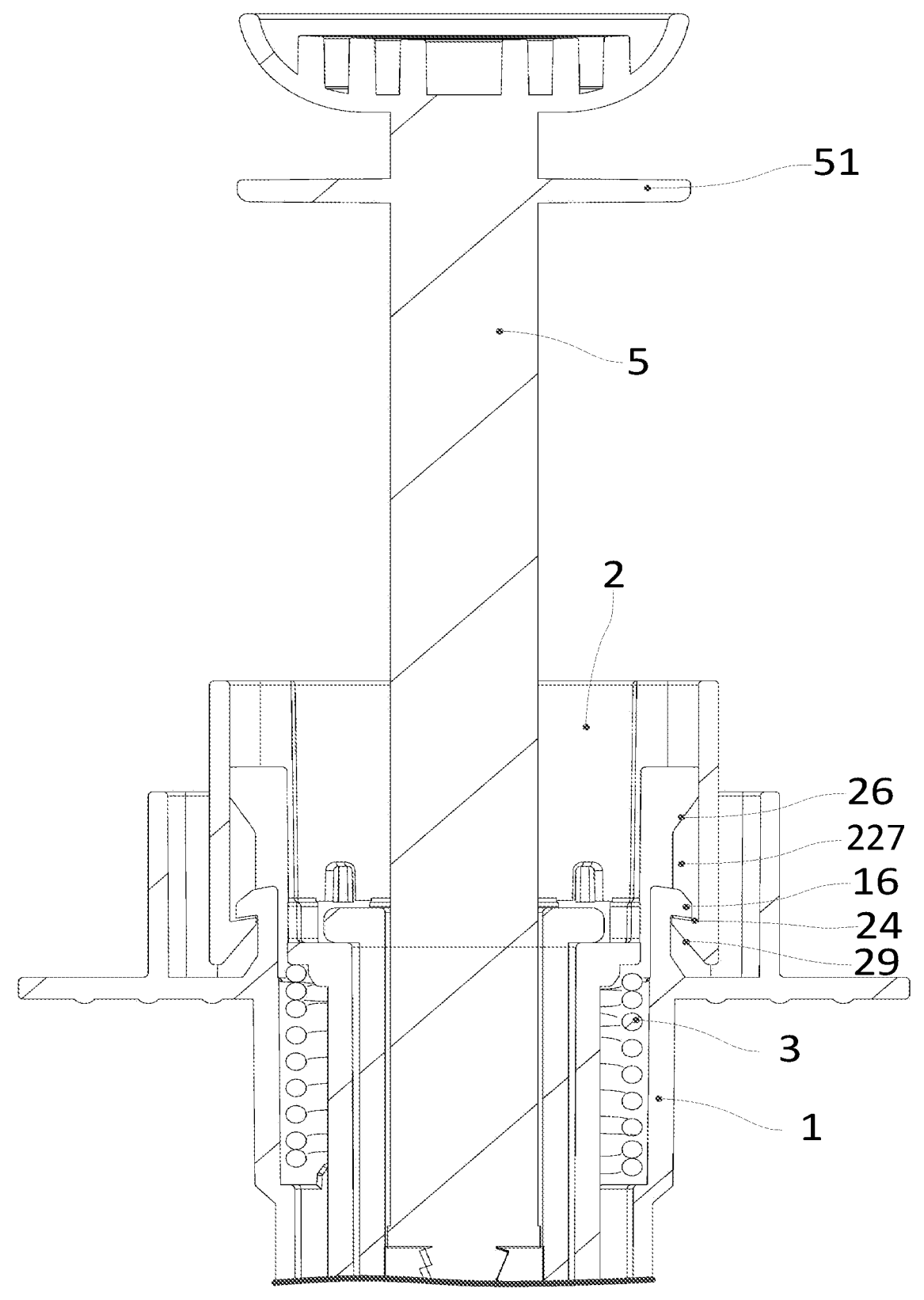
FIG. 20 is schematic diagram of the locking status of the safety snap joint of embodiment 1 of the snap joint of the disclosure.
Figure 21:
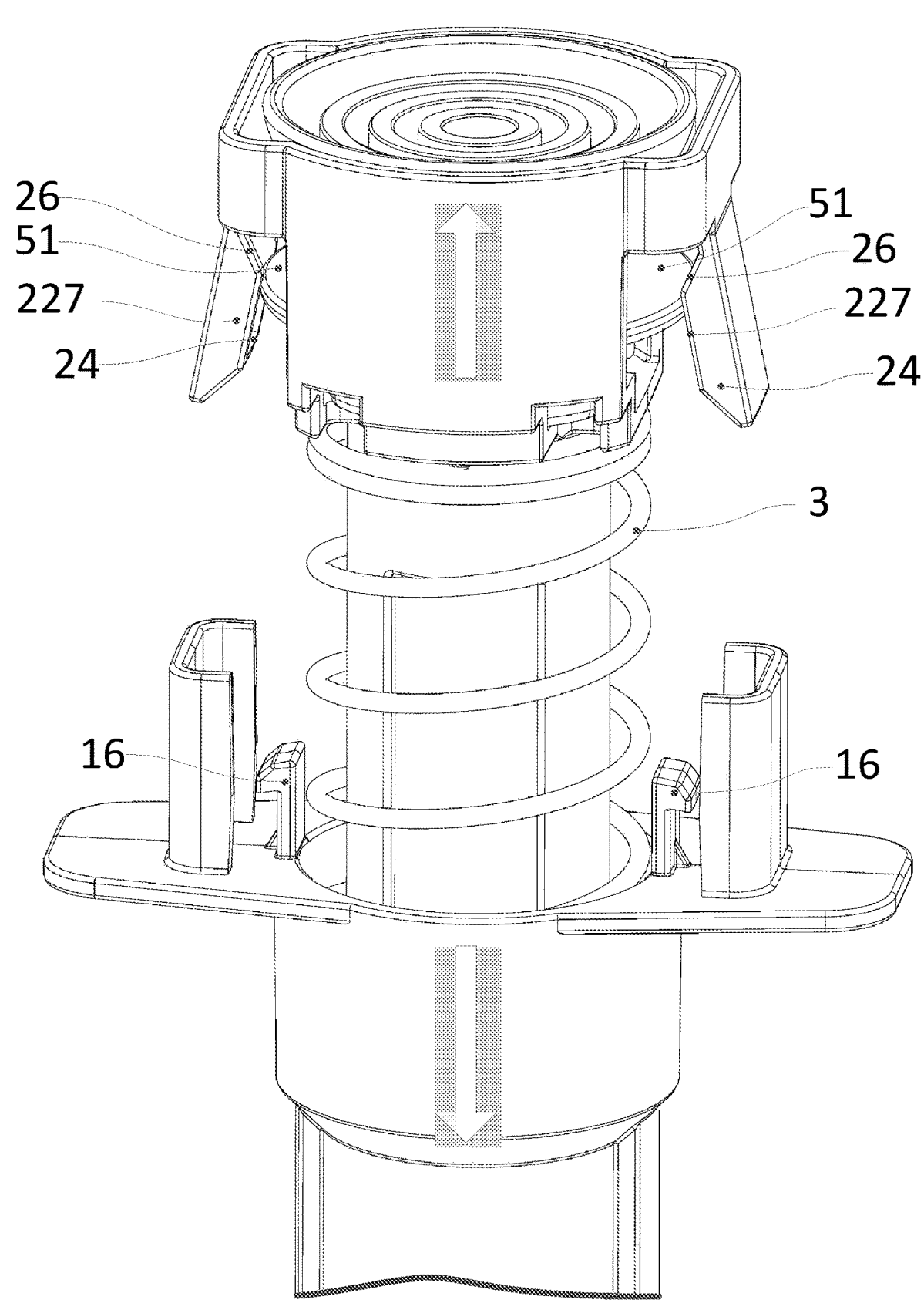
FIG. 21 is schematic diagram of the activation status of the snap joint of embodiment 1 of the safety snap joint of the disclosure.
Figure 22:
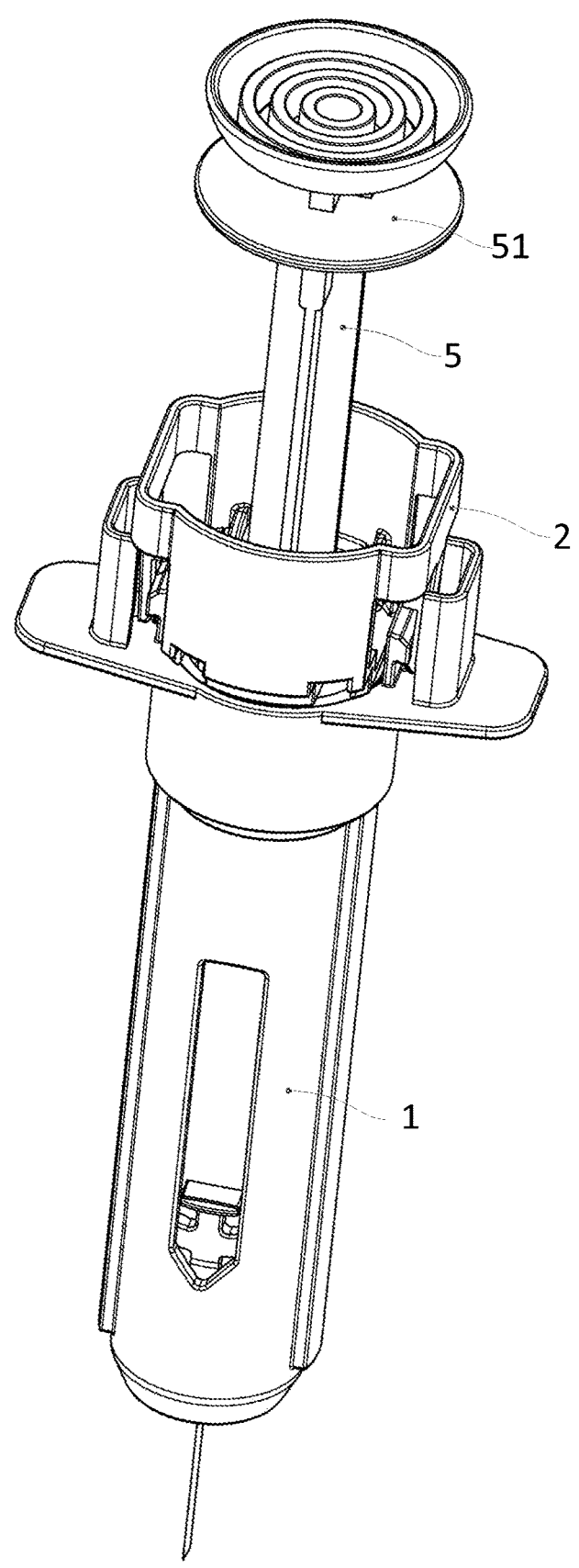
FIG. 22 is schematic diagram 1 of overall structure of protector of embodiment 2 of the safety snap joint of the disclosure.
Figure 23:
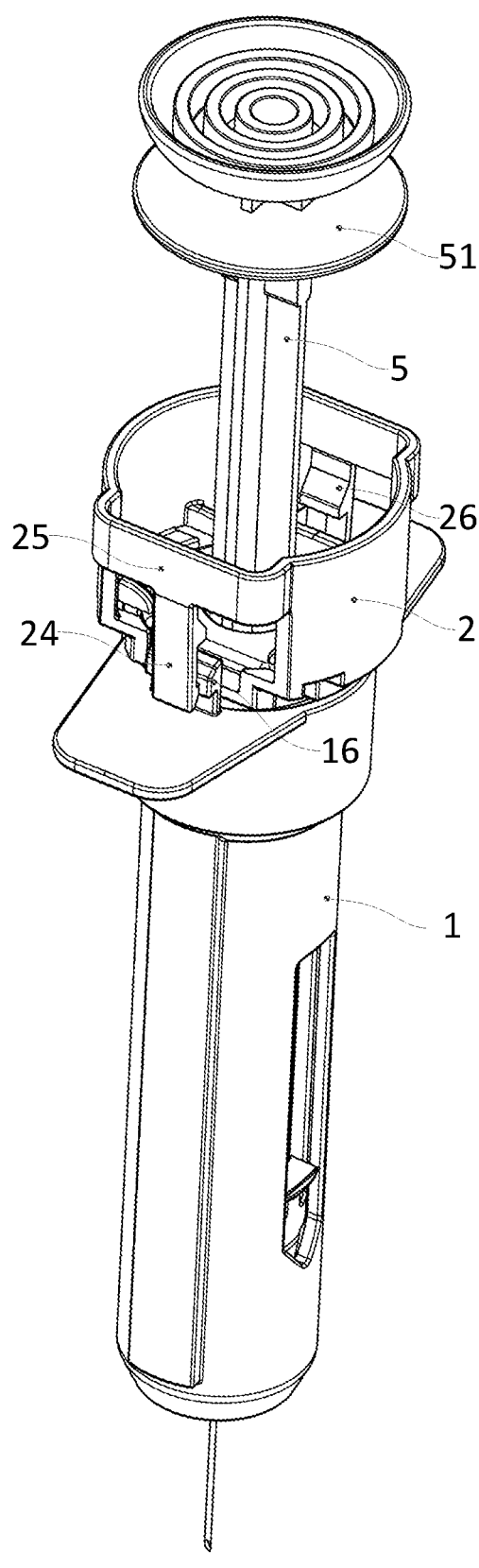
FIG. 23 is schematic diagram 2 of overall structure of the protector of embodiment 2 of safety snap joint of the disclosure.
Figure 24:
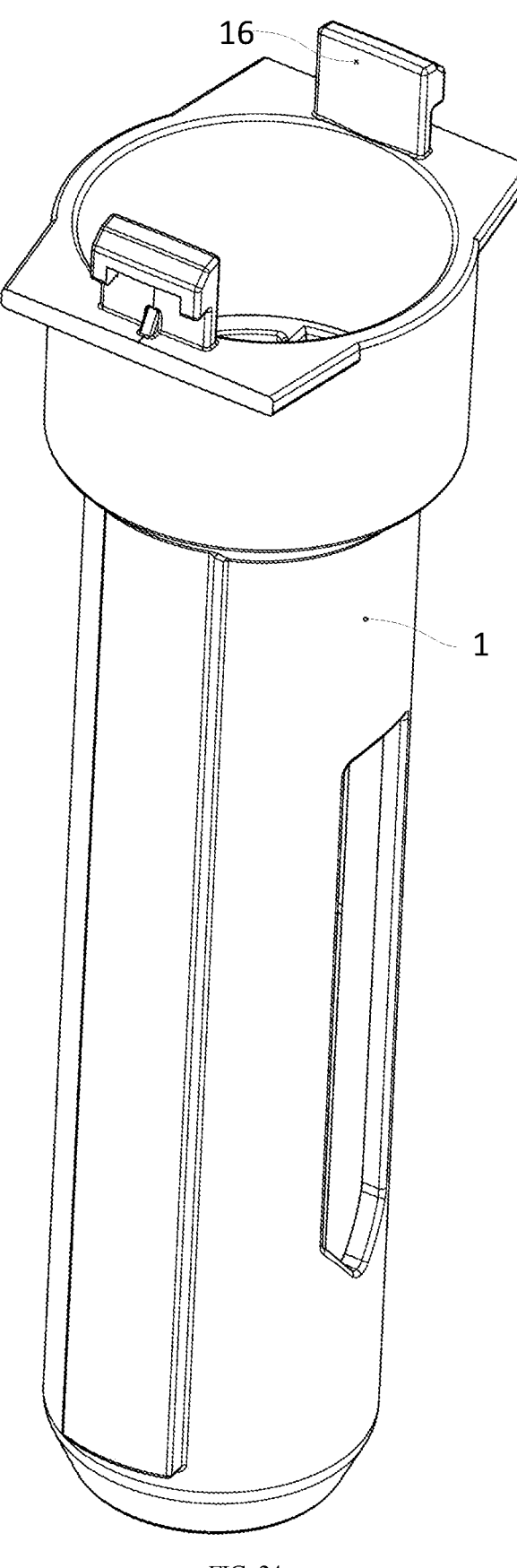
FIG. 24 is structure schematic diagram of the outer protection sleeve of embodiment 2 of safety snap joint of the disclosure.
Figure 25:
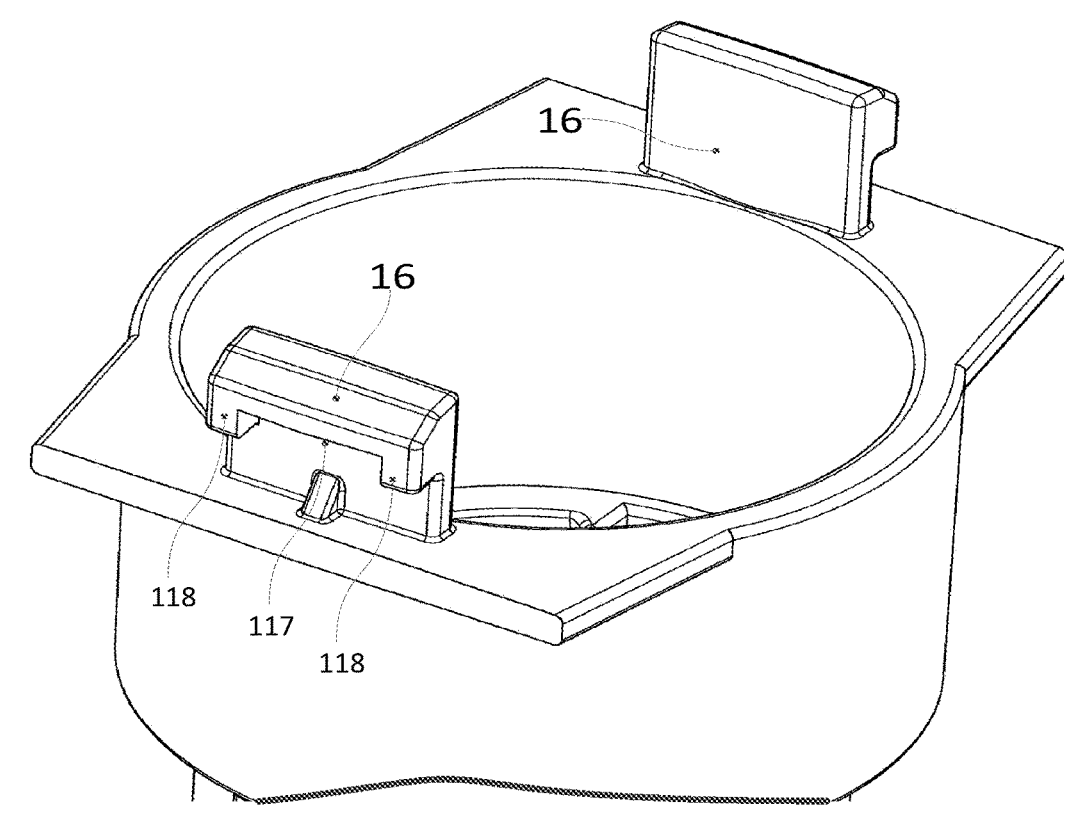
FIG. 25 is structure schematic diagram 1 of the inner locking jack catch of embodiment 2 of the safety snap joint of the disclosure.
Figure 26:
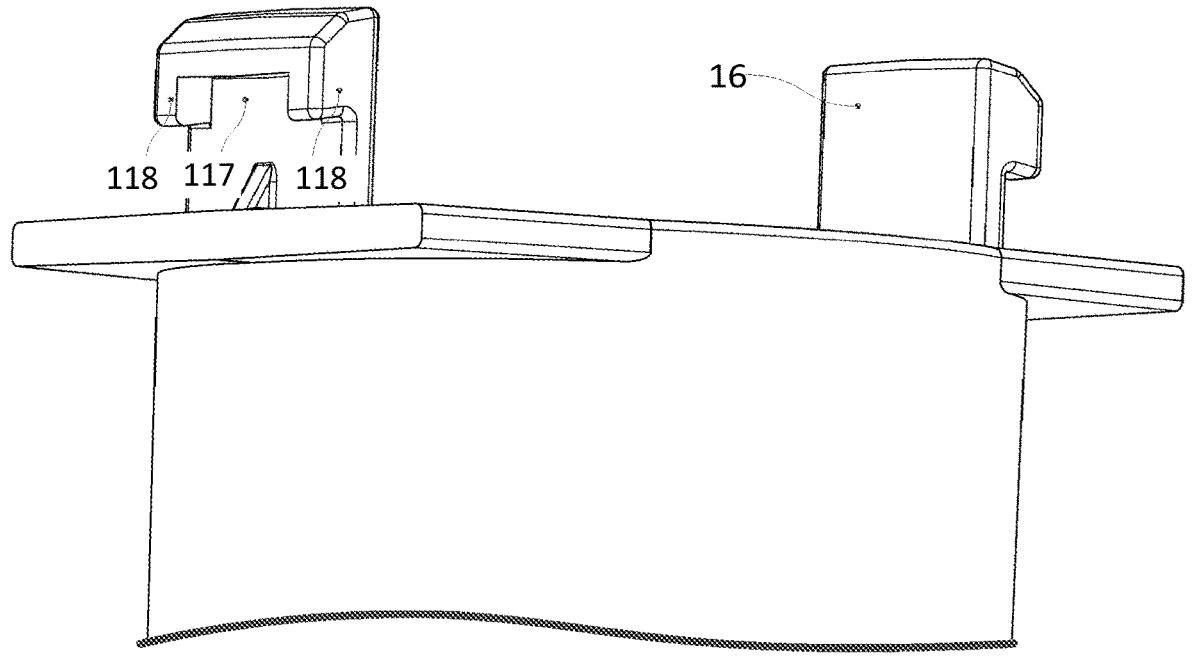
FIG. 26 is structure schematic diagram 1 of the inner locking jack catch of embodiment 2 of the safety snap joint of the disclosure.
Figure 27:
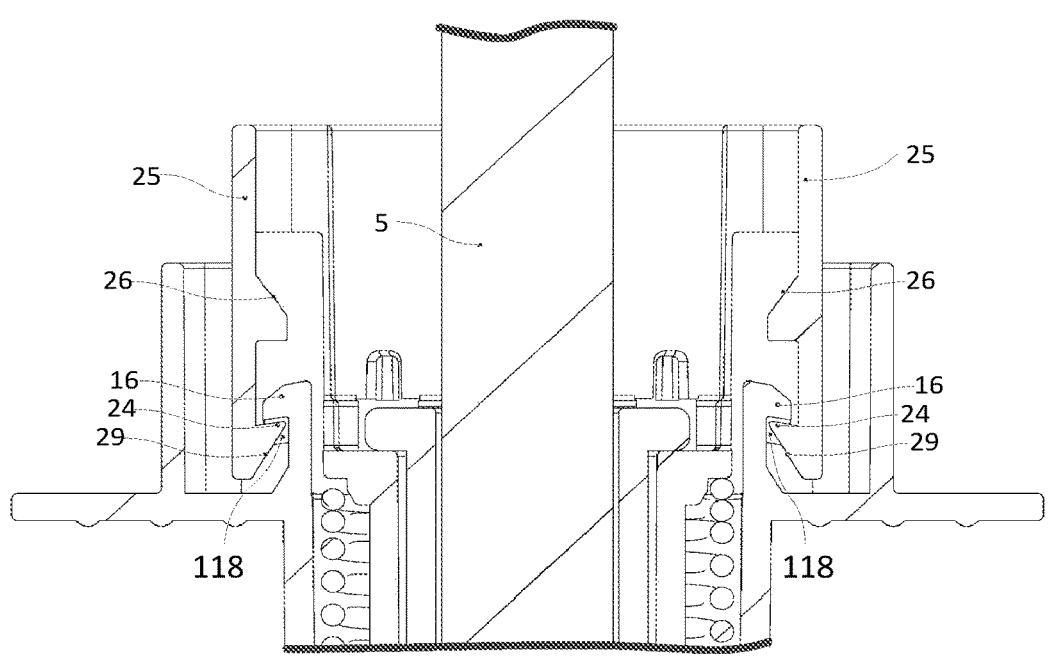
FIG. 27 is section view of locking status of the snap joint structure of embodiment 2 of the safety snap joint of the disclosure.
Figure 28:
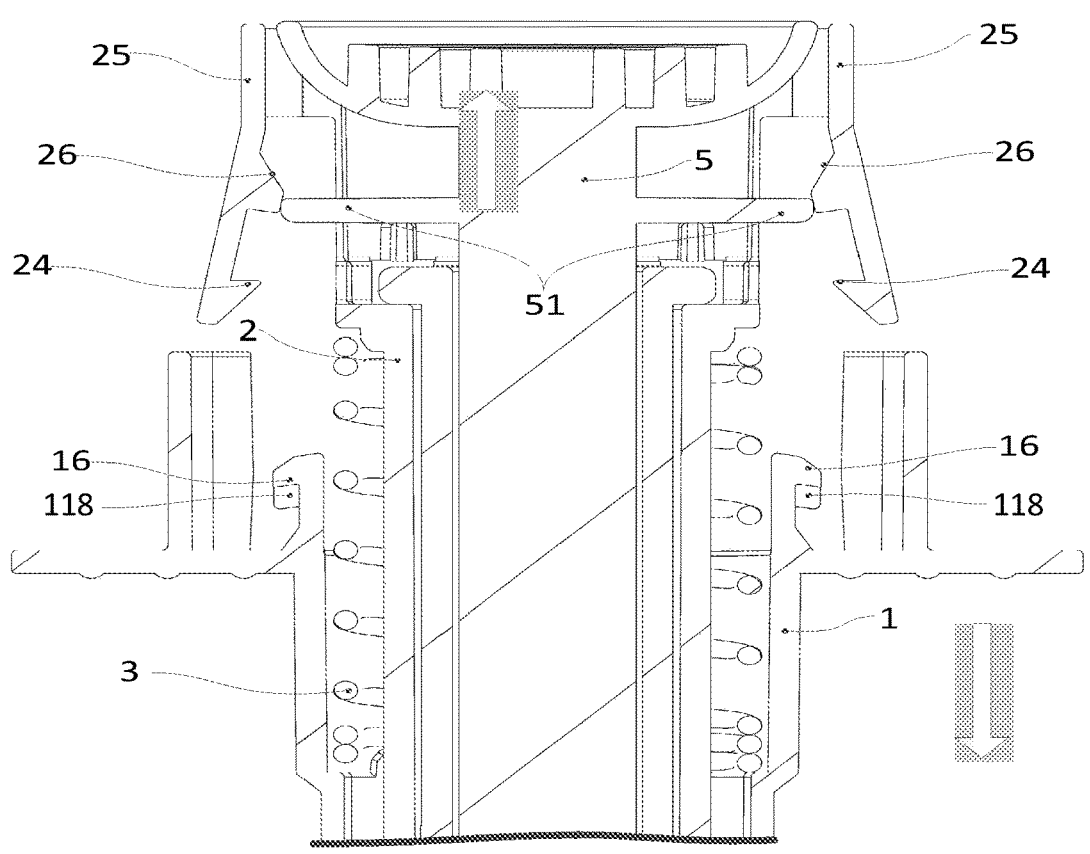
FIG. 28 is the section view of the activation status of the snap joint structure of embodiment of the safety snap joint of the disclosure.
Figure 29:
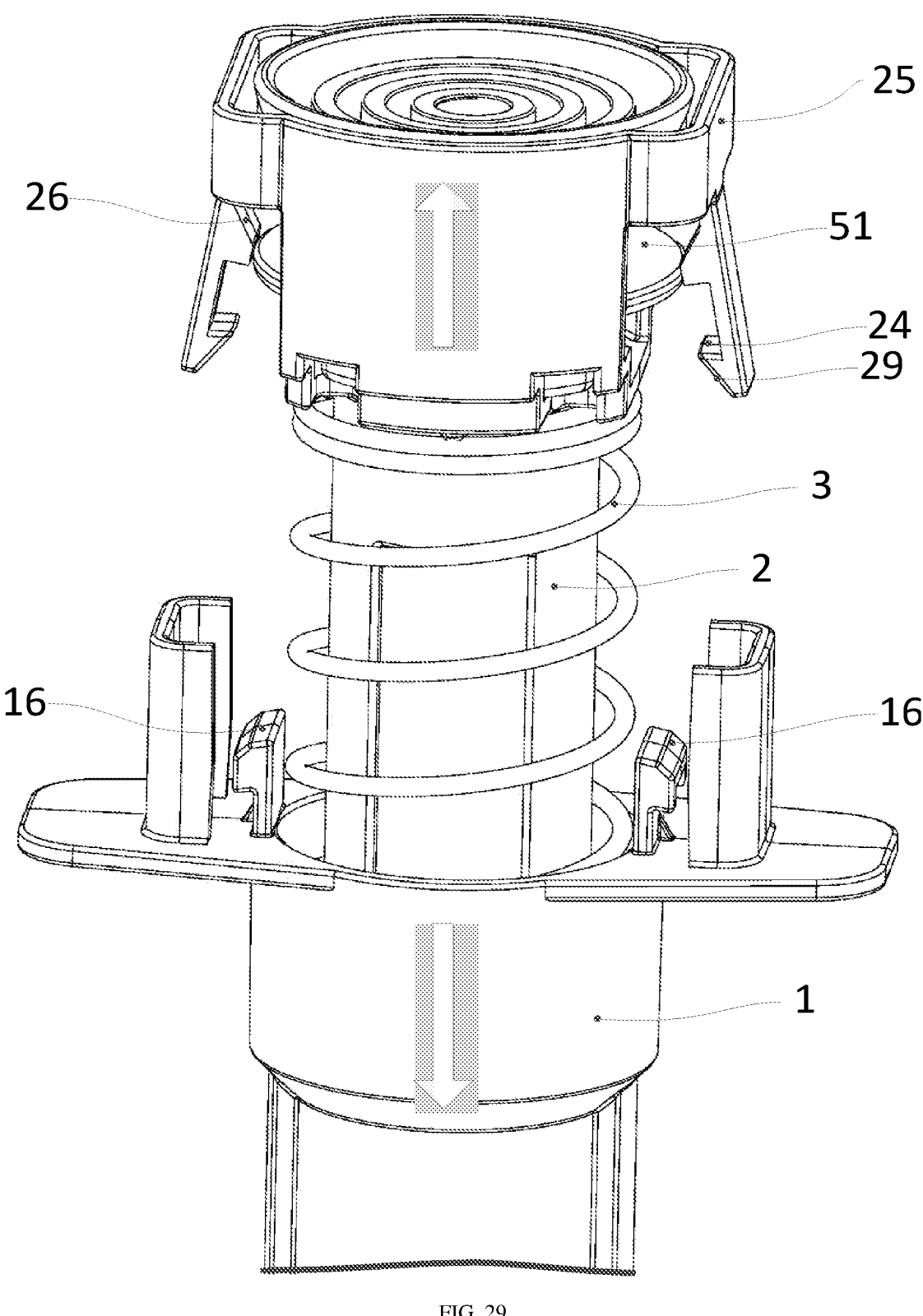
FIG. 29 is local schematic diagram of activation status of the snap joint structure of embodiment 2 of the safety snap joint of the disclosure.

As shown in FIG. 13-FIG. 15, the said spring starts releasing, the said outer protection sleeve 1 and the said outer installation sleeve 2 move relatively to the longest status; as shown in FIG. 13 and FIG. 15, at this moment, the said guide block 23 slides to the top of the said guide chute 13 to prevent separation between the said outer protection sleeve 1 and the said inner installation sleeve 2; meanwhile, as shown in FIG. 14, the said backstop jaw 22 flicks and is clipped into the said inner stop orifice 14 to prevent re-contracting between the inner protection sleeve 1 and the said inner installation sleeve 2 to expose the needle 6.

In terms of the syringe protector of the disclosure, the said inner locking jack catch 16 and the said outer locking jack catch 24 are interlocked and fastened, and the spring 3 is compressed to store energy; after the syringe protector has been assembled separately, in the process of use, the syringe is installed at the said inner installation sleeve 2 of the said syringe protector, the said syringe cam 41 is clipped into the said cam fixing groove 29, which is locked by the said syringe cam fixing jaw 28; then, remove the needle sleeve 7 and expose the needle 6 for injection; in the process of injection, push the piston rod 5 to push the medicine; at the end of finishing the medicine, the piston rod 5 flicks the said outer locking jack catch 24 and is separated from the said inner locking jack catch. The releasing and activation piece 51 is clipped into the piston fixing step 27 to fix the piston rod 5; after the medicine pushing is finished, the operator releases the syringe and the syringe protector, the spring 3 starts releasing, the said outer protection sleeve 1 and the said inner installation sleeve move relatively, and the said outer sleeve pipe orifice 11 is used to shield and protect the needle.

In terms of the syringe protector of the disclosure, the said outer protection sleeve 1 and the said inner installation sleeve 2 are made of plastics, in particular to parts related to the said inner installation sleeve 2, such as the said needle sleeve backstop piece 21, backstop jaw 22, connecting bar 231, outer locking jack catch 24 and syringe cam fixing jaw of great resilience, which shall be wrapped and reset elastically at different stages. The syringe protector of the disclosure has a simple structure. After the corresponding safety syringe has been used, the needle 6 can be well protected.

Safety Snap Joint

The disclosure improves the snap joint structure of the syringe protector to shape the safety snap joint.

The snap joint is comprised of an inner locking jack catch 16 and an outer locking jack catch. The said inner locking jack catch 16 is located on the outer protection sleeve 1 and is arranged upwards, inside the snap joint structure, and the jack catch is arranged outwards.

The said outer locking jack catch 24 is arranged on the inner installation sleeve 2 and is arranged below the jack catch frame 25, outside the snap joint structure of the said outer locking jack catch, which is located inwards; the said outer locking jack catch 24 rotates towards the said jack catch frame 25 along the stress edge and is separated from the said inner locking jack catch 16 to activate the syringe protector.

Embodiment 1 of the Safety Snap Joint:
Improvement of Outer Locking Jack Catch
Structure As shown in FIG. 16-FIG. 21, compared with the prior art, related structures of the outer locking jack catch 24 are improved to shape a snap joint with safe limit.

The said outer locking jack catch is 24 is installed with a jack catch surface fastened with the said inner locking jack catch 16, an inner jack catch limit body 227 is arranged on both sides of the said outer jack catch 24, and the inner jack catch storage groove 228 is located between the said inner jack catch limit body 227 on both sides; under locking status, the said inner jack catch 16 is located in the said inner jack catch storage groove 228; the said inner jack catch limit body 227 limits the left and right direction of the said inner locking jack catch 16.

A releasing slope 26 is arranged above the said inner jack catch limit body 227. When the syringe protector is to be activated, the piston rod 5 pushes the medicine, releasing and activation piece 51 approaches the said outer locking jack catch 24, finally, the said releasing and activation piece 51 contacts the said releasing slope 26 and moves downwards along the said releasing slope 26, moves the said outer locking jack catch 24 to make it rotate outwards, the said inner locking jack catch 16 leaves the said inner jack catch storage groove 28 and is separated from the said outer locking jack catch 24; the said releasing and activation piece 51 is clipped on the said inner jack catch limit body 227 to make the said outer locking jack catch 24 keep flicked; at this moment, the operator releases the hand, the spring 3 acts to make the said outer protection sleeve 1 and the said inner installation sleeve far away to activate the syringe protector.

An outer jack catch guide slope 29 is located at the bottom of the said outer locking jack catch, a guide slope is arranged on the top of the corresponding said inner locking jack catch 16, both slopes cooperates for easy assembly, namely the said outer protection sleeve 1 and the said inner installation sleeve 2 are extruded, the top of the said inner locking jack catch 16 pushes the said outer locking jack catch along the said outer jack catch guide slope 29, the snap joint of the said inner locking jack catch 16 falls into the said inner jack catch storage groove 228, and the said outer locking jack catch 24 is recovered elastically to finish the assembling.

In the embodiment, the said inner jack catch limit body 227 is arranged on both sides of the outer locking jack catch 24, an inner jack catch storage groove 228 is formed, under normal status, the said inner locking jack catch 16 is clipped in the said inner jack catch storage groove 228 to form safety snap joint with safety limit, the left and right directions of the said inner locking jack catch 16 are prevented, the said outer protection sleeve 1 and the said inner installation sleeve 2 will not be deflected by external stress, the said inner locking jack catch 16 and the said outer locking jack catch 24 are separated to activate by mistake.

Embodiment 2 of the Safety Snap Joint:
Improvement of the Inner Locking Jack Catch
Structure As shown in FIG. 22-FIG. 29, compared with the prior art, relevant structure of the inner jack catch 16 is improved to finish a snap joint with safety limit structure.

The said inner locking jack catch 16 is arranged with an inner jack catch surface 117 fastened with the said outer locking jack catch; the improvement of the embodiment is that, both sides of the said inner jack catch surface 117 are arranged with the outer jack catch limit body 118; under locking status, the jack catch surface of the said locking outer jack catch 24 is clipped between the outer jack catch limit body 118 on both sides and fastened with the said inner jack catch surface, and the said outer jack catch limit body 118 is used to limit the left and right directions of the said outer locking jack catch 24.

A slope is installed outside the said inner locking jack catch 16 in the upper portion and is cooperated with the outer jack catch guide slope 29 of the said outer locking jack catch 24.

When the safety snap joint of the embodiment is activated and released, the piston rod 5 pushes the medicine to release the activation piece 51 and approach the said outer locking jack catch 24, the said releasing and activation piece 51 contacts the said releasing slope 26, moves downwards along the said releasing slope to move the said outer locking jack catch, the said outer locking jack catch 24 rotates outwards along the connection of the jack catch frame 25, the said locking outer jack catch 25 leaves the said outer jack catch limit body 118 progressively, and is thoroughly separated from the said inner locking jack catch 16; finally, the operator releases hand, the spring 3 acts to make the said outer protection sleeve 1 and the said inner installation sleeve 2 far away to activate the syringe protector.

In the embodiment, an outer jack catch limit body 118 is used to limit the said outer locking jack catch 24 to shape a snap joint with safe limit and ensure that the said outer protection sleeve 1 and the said inner installation sleeve 2 will not be deflected by external stress, and the said inner locking jack catch 16 and the said outer locking jack catch 24 are separated to activate by mistake.

Embodiment 3 of the Safety Snap Joint: Improvement of the Inner Locking Jack Catch and the Outer Locking Jack Catch As shown in FIG. 30-FIG. 36, compared with the prior art, related structures of the inner locking jack catch 16 and the outer locking jack catch 24 are improved to shape a snap joint with safe limit.

Figure 30:
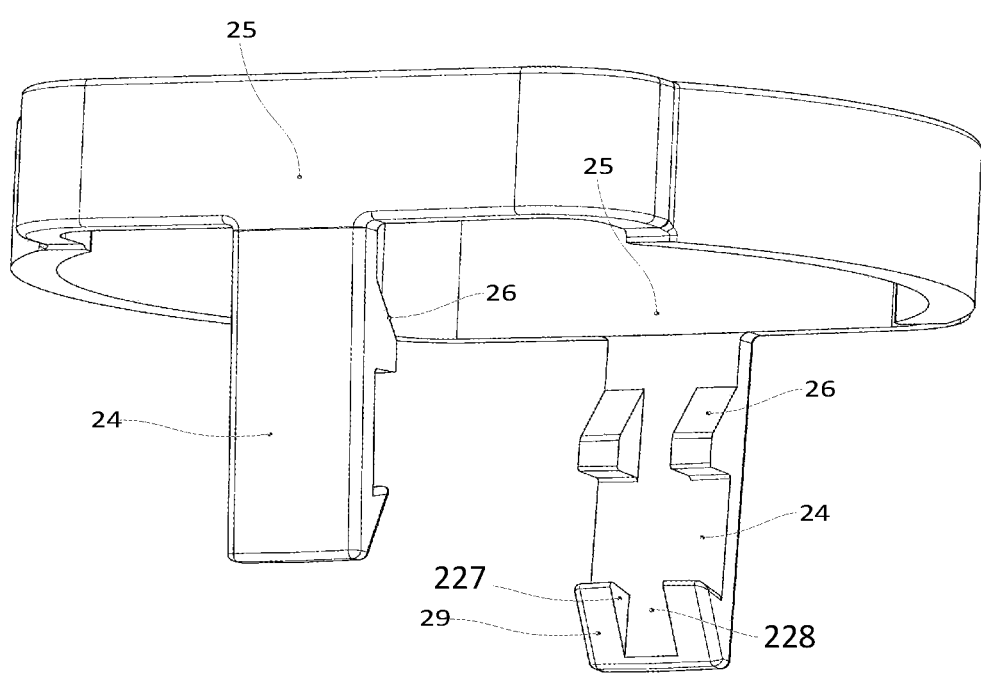
FIG. 30 is structure schematic diagram 1 of outer locking jack catch of embodiment 3 of the safety snap joint of the disclosure.
Figure 31:
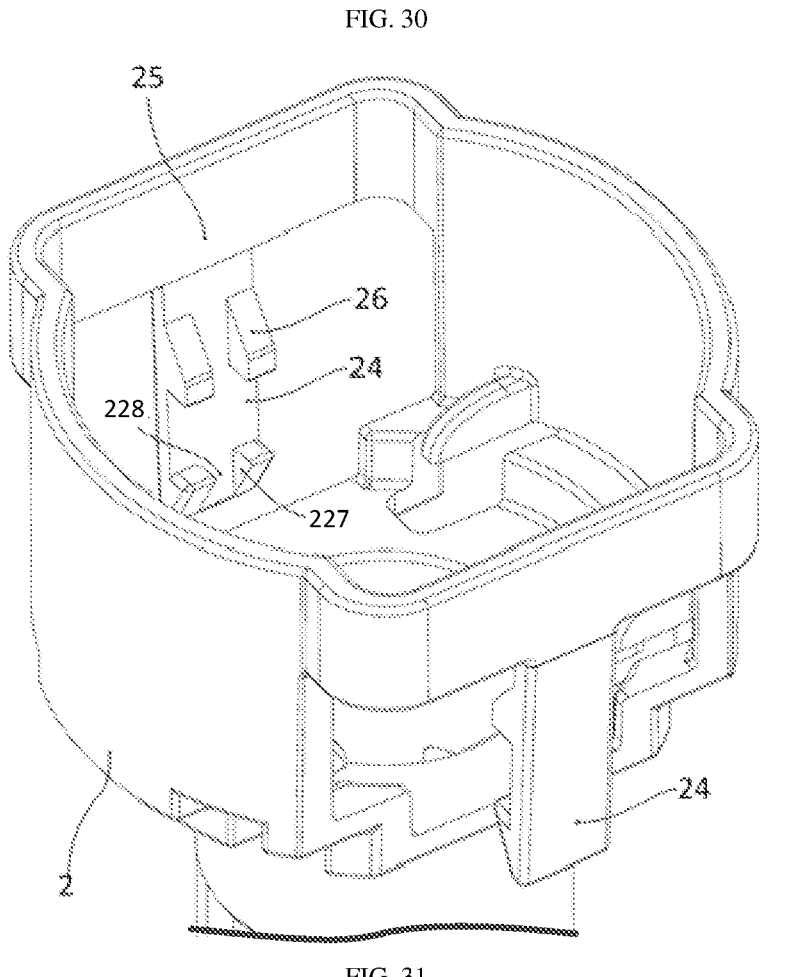
FIG. 31 is structure schematic diagram 2 of outer locking jack catch of embodiment 3 of the safety snap joint of the disclosure.
Figure 32:
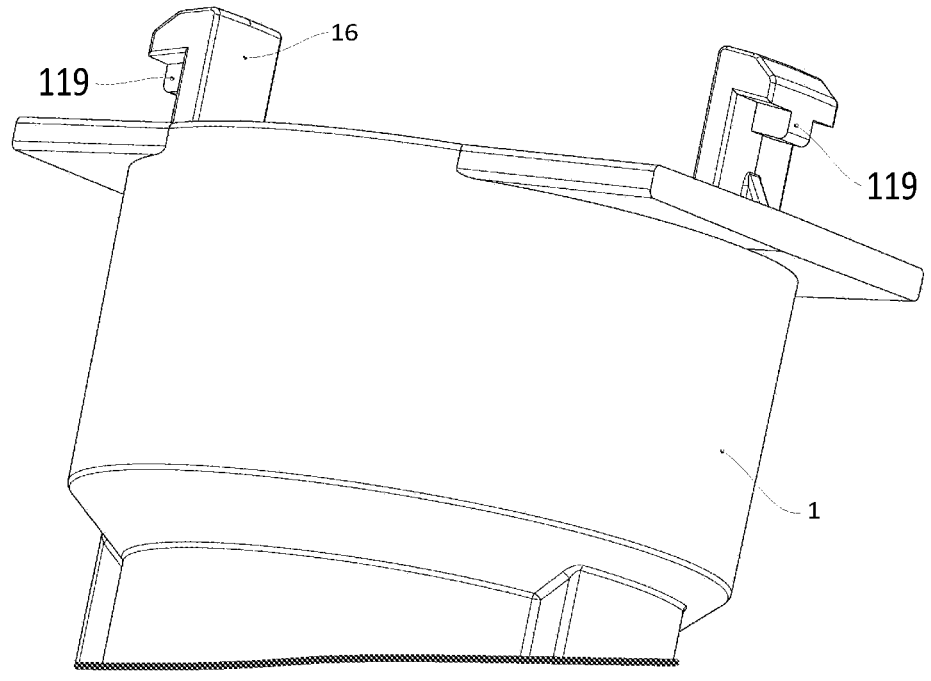
FIG. 32 is the structure schematic diagram of the inner locking jack catch of embodiment of the safety snap joint of the disclosure.
Figure 36:
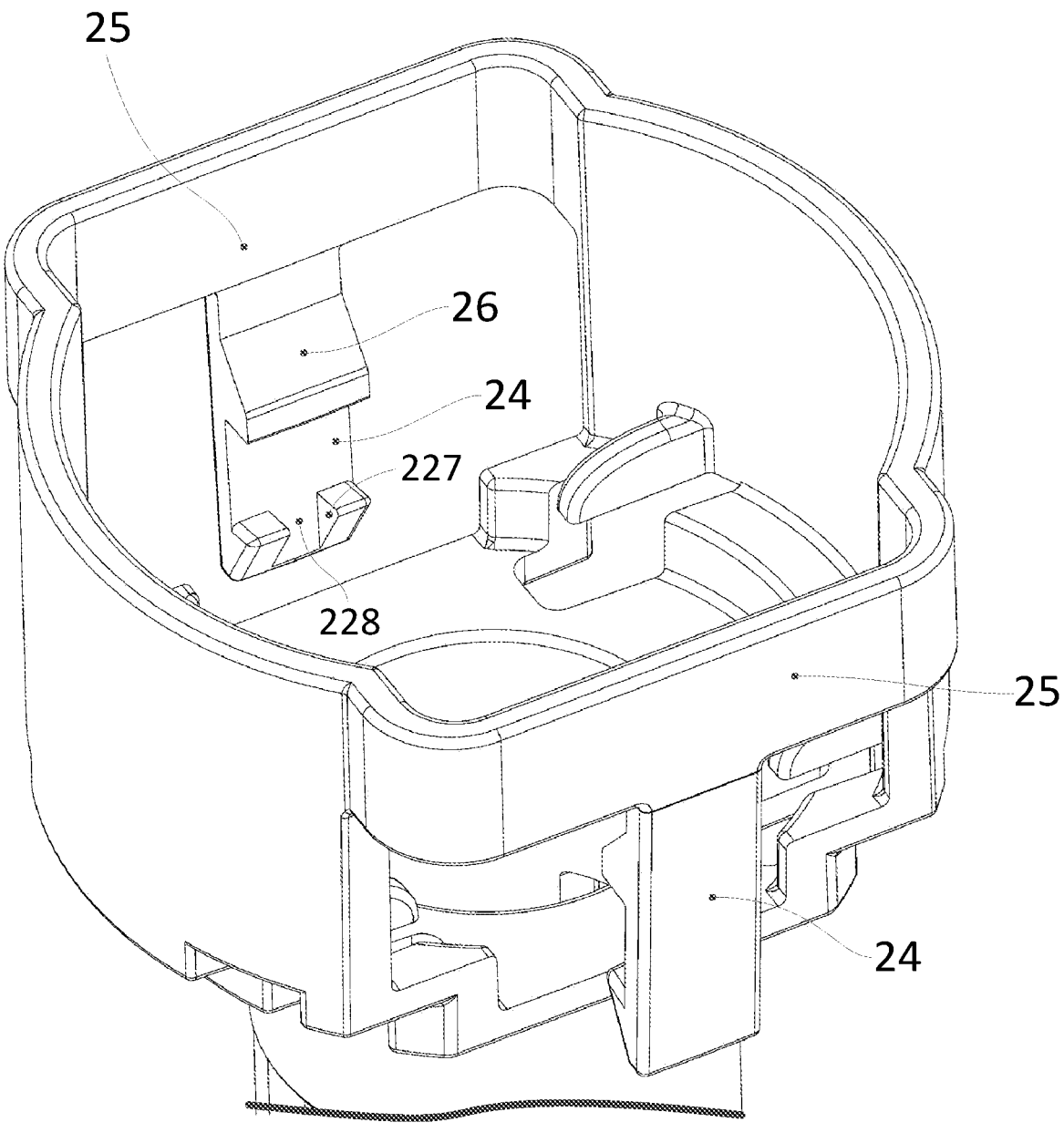
FIG. 36 is structure schematic diagram 3 of outer locking jack catch of embodiment 3 of safety snap joint of the disclosure.

A groove is made in the middle of the jack catch body of the said outer locking jack catch to form the inner jack catch storage groove 228, and the inner jack catch limit body 227 on both sides. For easy manufacturing, a groove (as shown in FIG. 30 and FIG. 31) which is communicated with the said inner locking jack catch storage groove is made in the middle of the said releasing slope 26, or no groove is made on the said releasing slope 26, which is a continuous integrity (as shown in FIG. 36).

A convex inner jack catch protrusion 119 is located at the lower portion in the middle of the jack catch body of the said inner locking jack catch 16; width of the convex inner jack catch protrusion 119 matches width of the said inner jack catch storage groove.

Figures 33, 34:
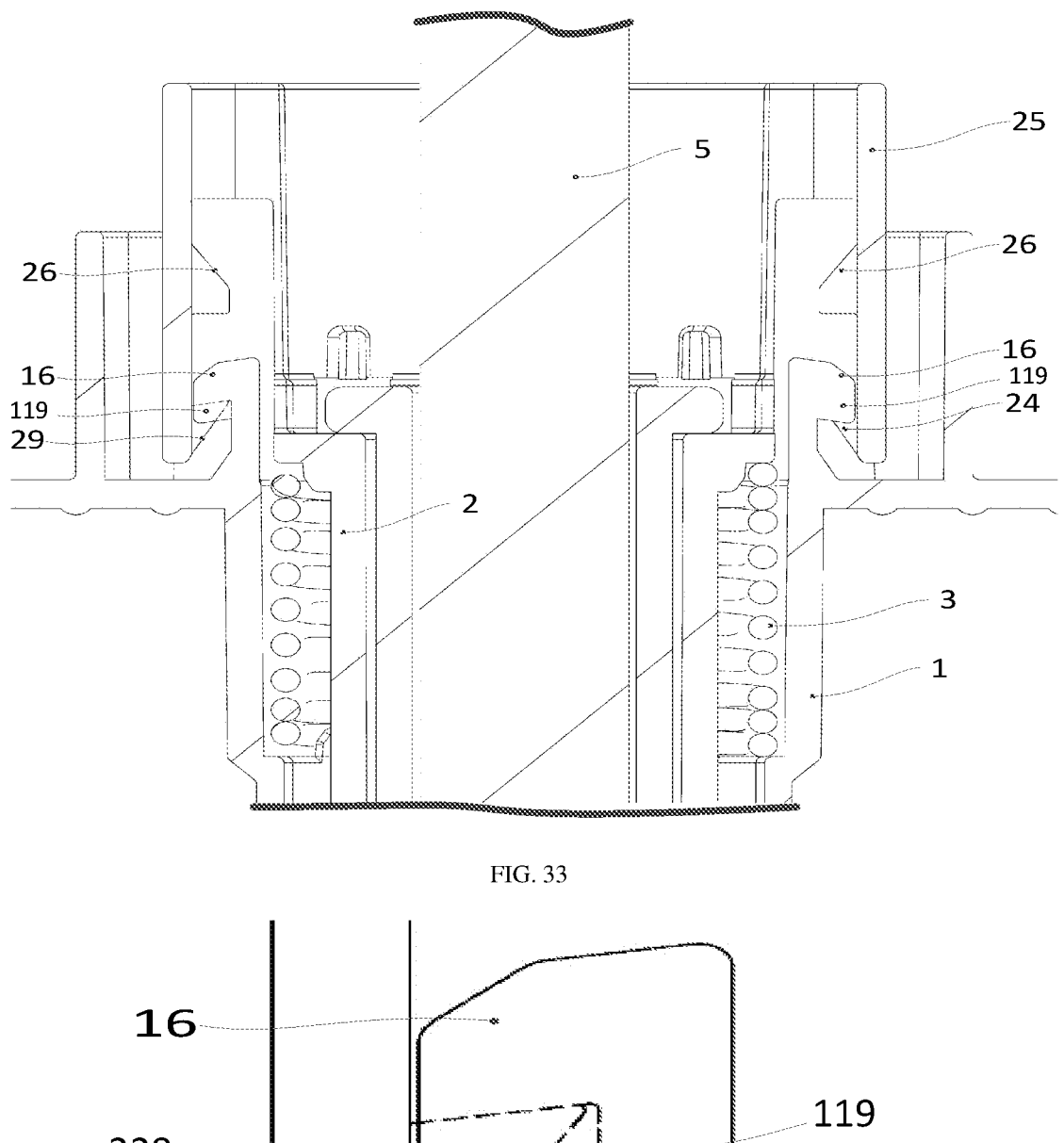
FIG. 33 is section view of locking status of the snap joint structure of embodiment 3 of the safety snap joint of the disclosure.
FIG. 34 is local enlarged schematic diagram of snap joint structure locking status of embodiment 3 of the safety snap joint of the disclosure.
Figure 35:
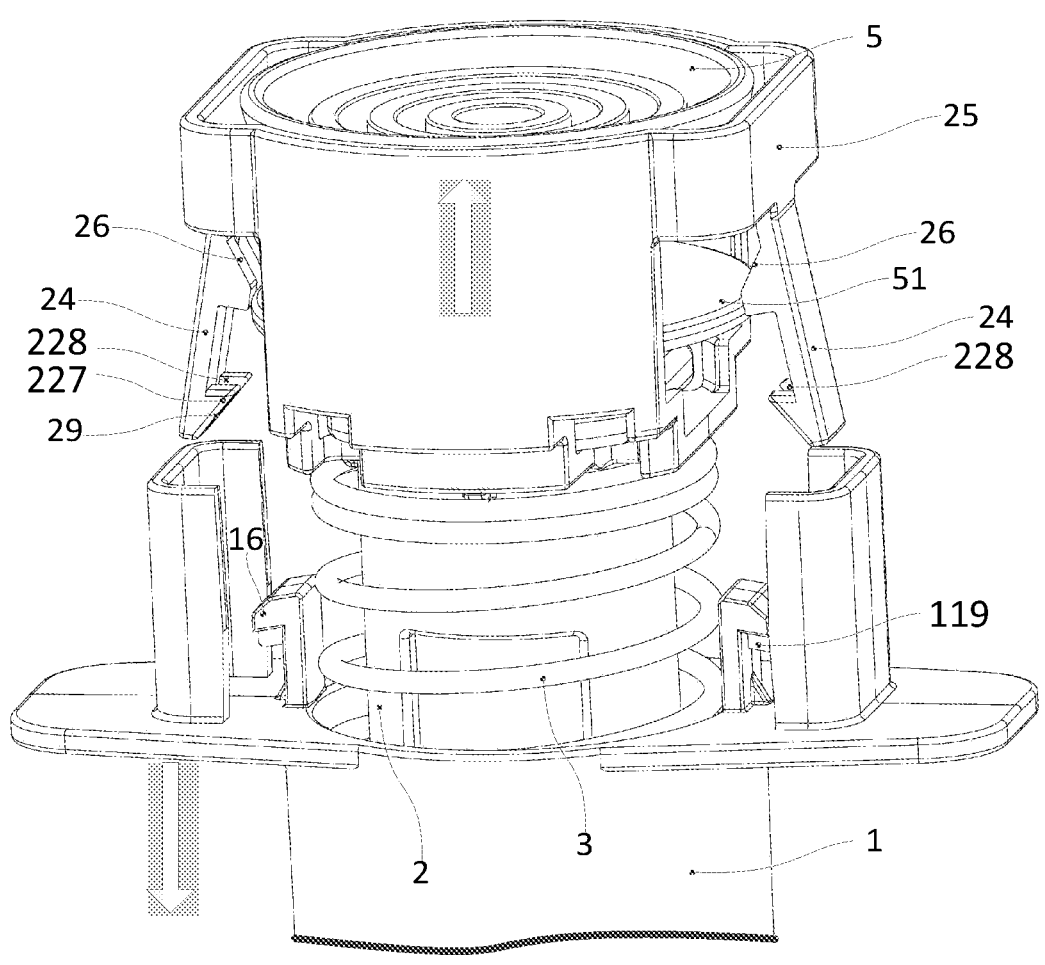
FIG. 35 is local schematic diagram of activation status of the snap joint structure of embodiment 3 of the safety joint of the disclosure.

As shown in FIG. 33 and FIG. 34, under locking status of the safety snap joint of the disclosure, the said inner locking jack catch 16 contacts the said outer locking jack catch 24, in particular to the said inner jack catch protrusion 119 clipped into the said inner jack catch storage groove 228 to realize that the said inner locking jack catch 16 limits the said outer locking jack catch 24 at the left and right directions.

When the safe snap joint in the embodiment is activated and released, the piston rod 5 pushes medicine to release the activation piece 51 and approach the said outer locking jack catch; finally, the said releasing and activation piece 51 contacts the said releasing slope, moves downwards along the said releasing slope 26, moves the said outer locking jack catch 24 to make the connection of the said outer locking jack catch 25 along the jack catch 25 rotate outwards, the said outer locking jack catch 24 leaves the said outer jack catch limit body 118 progressively, in particular to separation of the said inner jack catch storage groove 28 and the said inner jack catch protrusion 119, then the said outer locking jack catch 24 and the said inner jack catch 16 are separated thoroughly; finally, the operator releases the hands, the spring 3 acts, the said outer protection sleeve 1 and the said inner installation sleeve 2 are far away to activate the syringe protector.

In the embodiment, an inner catch joint protrusion 119 and an inner catch joint storage groove 228 are used to form a mutually fastened concave and convex limit structure, thus form a snap joint with safe limit, ensure that the said outer protection sleeve 1 and the said inner installation sleeve 2 will not be deflected by external stress, and the said inner locking jack catch 16 and the said outer locking jack catch 24 are separated to activate by mistake.

Embodiment of the Safety Snap Joint: Improvement of Inner Locking Jack Catch and Outer Locking Jack Catch Based on the embodiment 3, a groove is made in the middle of the said inner locking jack catch is made to form an outward jack catch storage groove, an outer jack catch protrusion is located below the center of the said outer locking jack catch and is clipped into the outer jack catch storage groove, which shape a mutually fastened convex and concave structure and shape a snap joint with safe limit.

A safe snap joint is formed through the left and right limit structure at the jack catch to ensure that the said outer sleeve 1 and the said inner installation sleeve 2 will not be deflected by external stress, the said inner locking jack catch 16 and the said outer locking jack catch 24 are separated to activate by mistake.

Safety Syringe Without Protrusion

Figure 37:
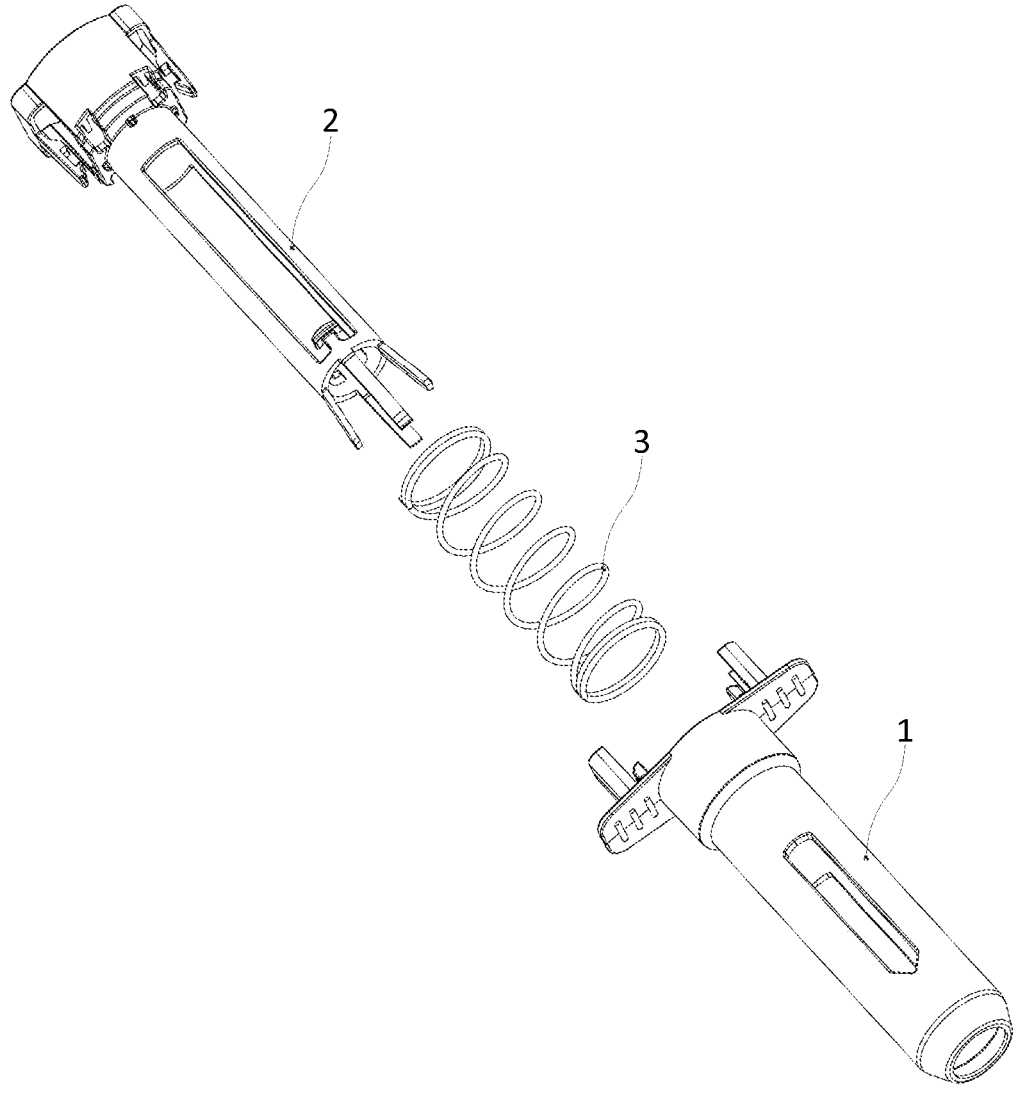
FIG. 37 is part explosive drawing of the protector without convex structure of the disclosure.

As shown in FIG. 37, the syringe protector without protrusion is comprised of an outer protection sleeve 1, an inner installation sleeve 2, and a spring 3, and the inner installation sleeve 2 is sleeved on the spring 3 and pressed in the said outer protection sleeve 1; in the process of use, the locking snap joint structure is opened, the spring 3 is released, the outer protection sleeve 1 and the inner installation sleeve 2 are flicked, and the outer protection sleeve 1 shields and protects the syringe needle within the inner installation sleeve 2.

Figure 38:
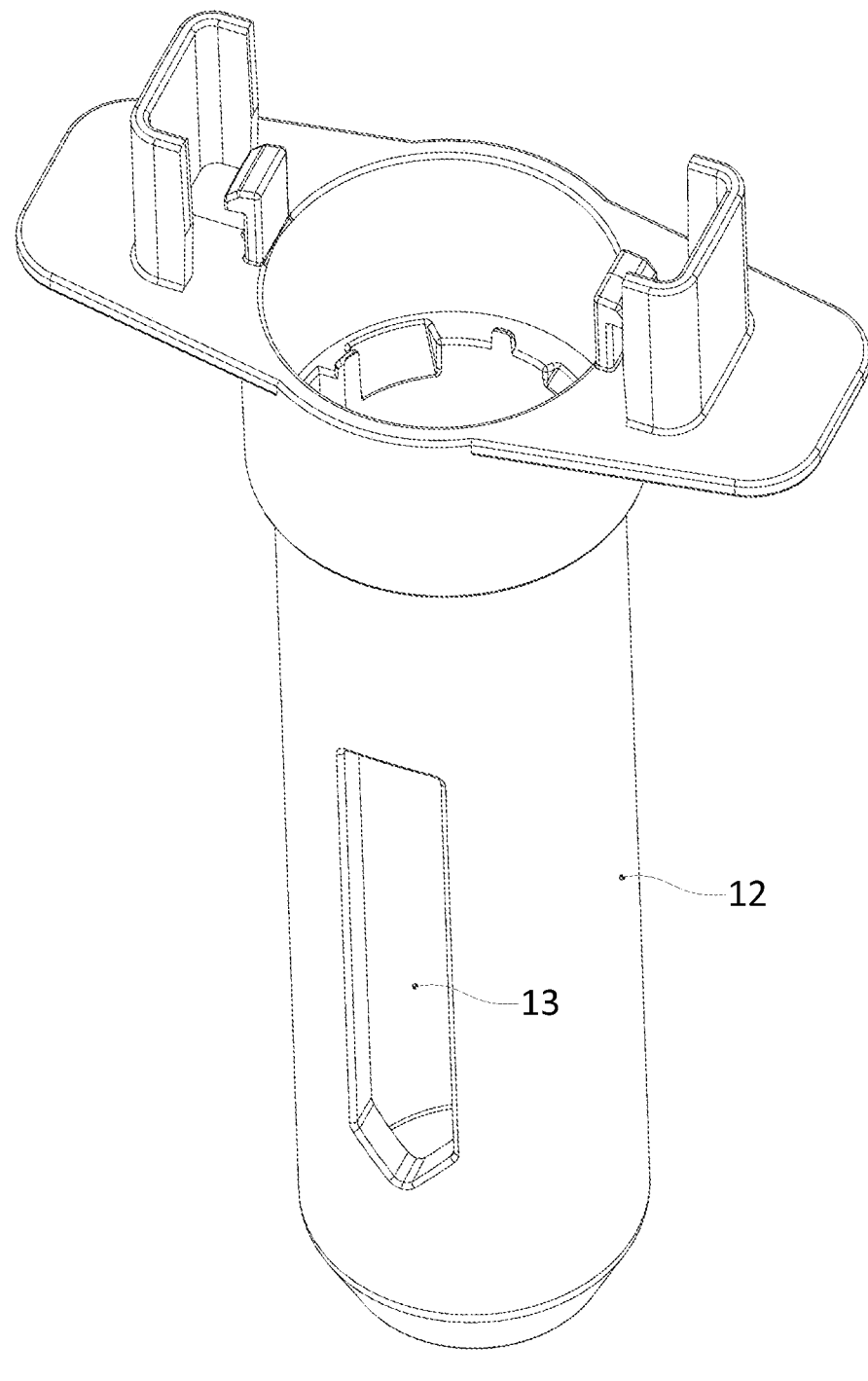
FIG. 38 is structure schematic diagram of the outer protection sleeve without convex structure of the disclosure.

As shown in FIG. 38, the outer surface of the outer sleeve tube body 12 of the said outer sleeve 1 is free of protrusion to form a continuous surface for sticking labels, or etching pictures or texts.

Figure 39:
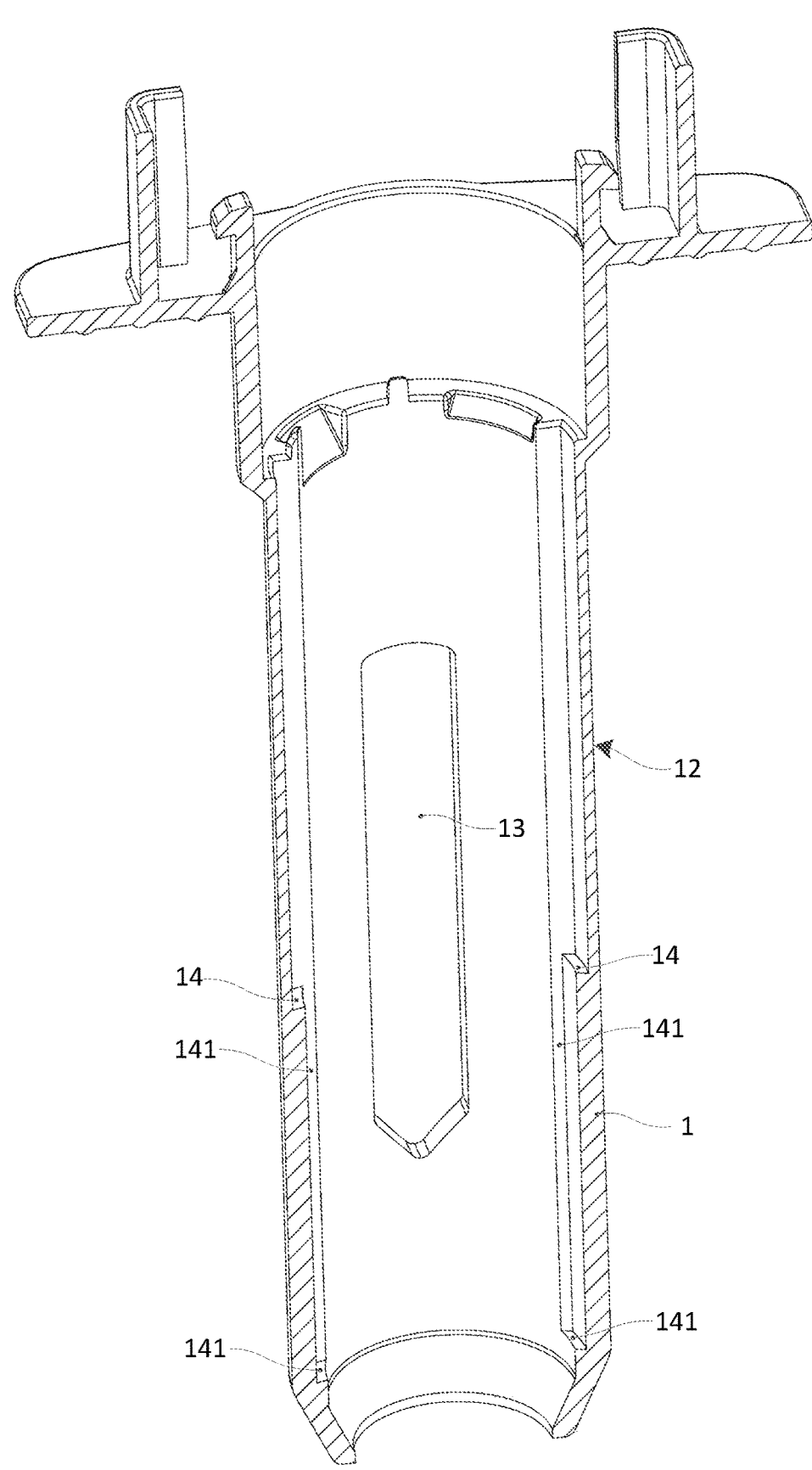
FIG. 39 is section view 1 of the outer protection sleeves without convex structure.
Figure 40:
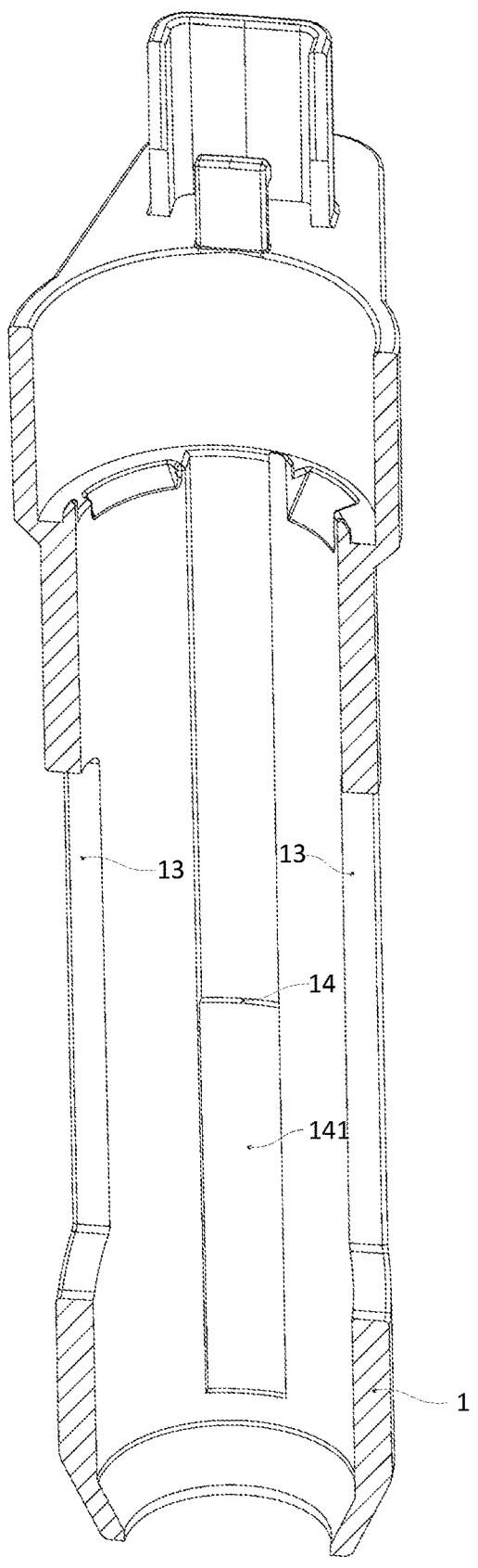
FIG. 40 is section view 2 of the outer protection sleeves without convex structure.
Figure 41:
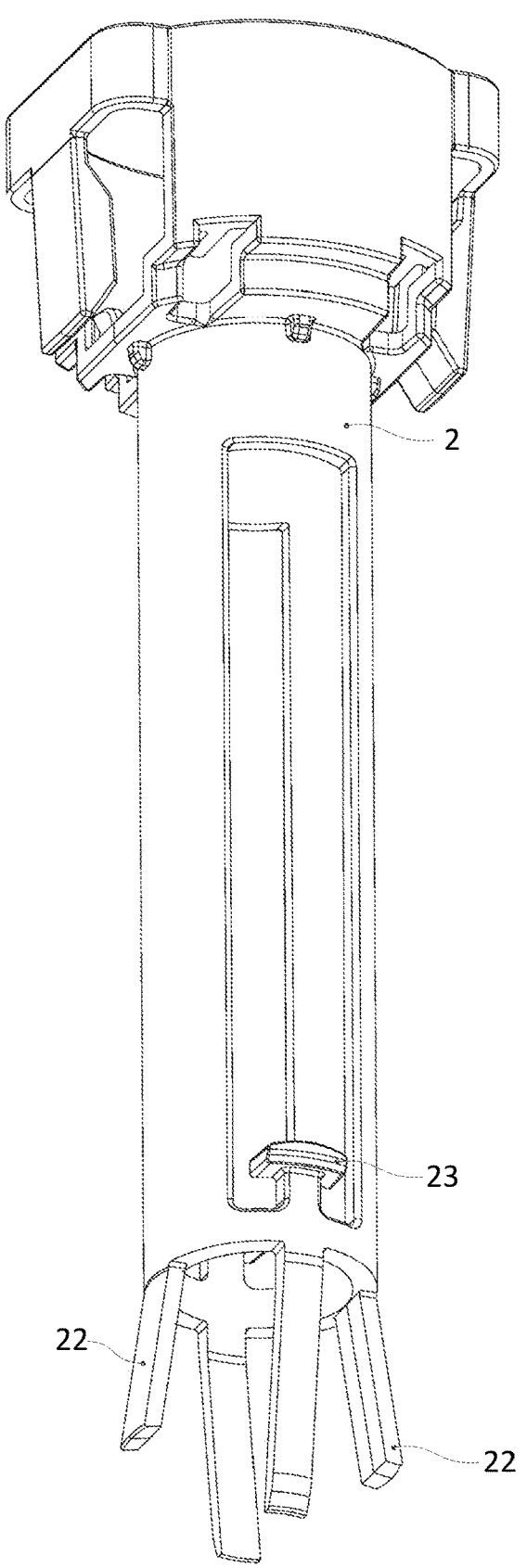
FIG. 41 is schematic diagram of structure of the inner installation sleeve without convex structure.

Further, as shown in FIG. 39 and FIG. 40, an inner stop orifice 14 is arranged inside the said outer protection sleeve 1 to obtain the outer sleeve cylinder 12 without protrusion, and wall thickness of the part shall be increased to form the inner stop orifice 14; further, an inner guide chute 141 is arranged on the longitudinal direction of the said inner stop orifice 14, and the said inner guide chute 141 extends downwards along the inner stop orifice 14 until near the outer sleeve pipe orifice.

The said outer protection sleeve 1 is installed with a guide chute 13; the guide chute 13 is through the wall surface of the said outer sleeve tube body 12 and is arranged inside the said outer sleeve tube body 12, not through the wall surface of the said outer sleeve body 12 to obtain a complete surface of a continuous and complete outer sleeve tube body 12 for sticking labels or etching pictures or texts.

The said inner installation sleeve 2, as shown in FIG. 40, is similar to the prior structure. A backstop jaw 22 is arranged at the bottom, and a guide block 23 is arranged; the said backstop jaw 22 flicks outwards, with elasticity.

Figure 42:
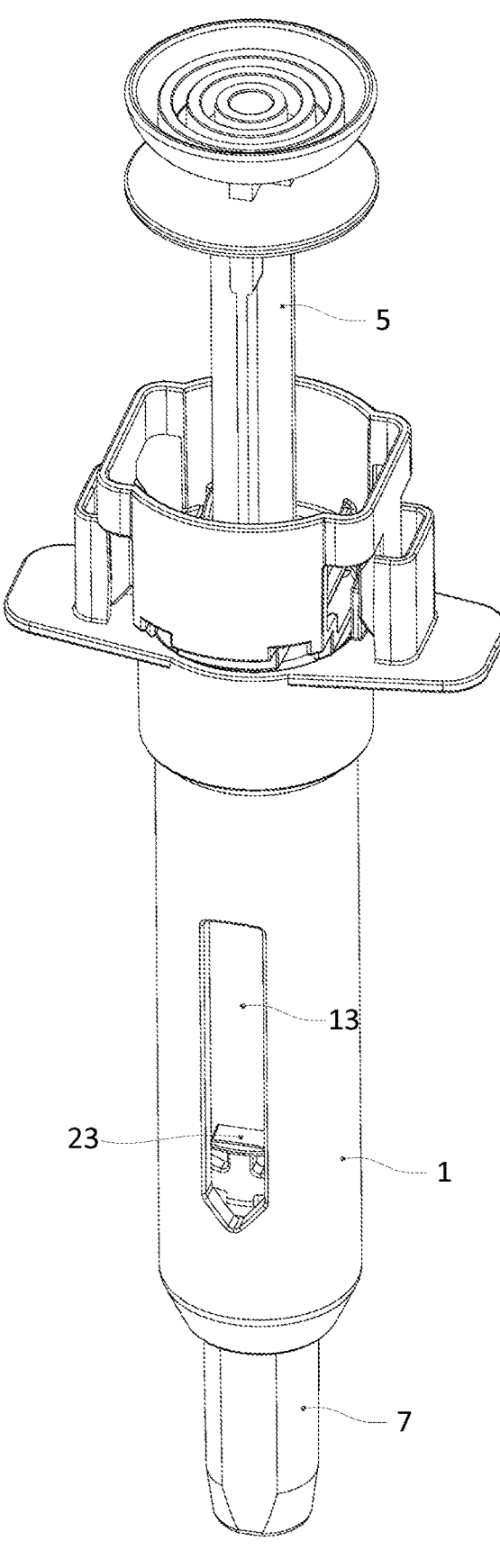
FIG. 42 is schematic diagram of assembling structure of the safety syringe without convex structure.

As shown in FIG. 42, after assembling of the syringe protector of the disclosure, the said guide block 23 is clipped into the said guide chute 13, and relative movement of the said outer protection sleeve 1 and the said inner installation sleeve 2 is guide and limited; to apply labels or etch pictures or texts on the outer surface of the said outer sleeve tube body, the said guide chute 13 is not through the wall surface of the said outer sleeve tube body 12; even if the said guide chute 13 is through the wall surface of the said outer sleeve tube body 12, the height of the said guide block 23 clipped into the said guide chute 13 is low, not protruding over the outer surface of the said outer sleeve tube body as much as possible. After the labels are stuck and the outer surface of the said guide chute 13 is covered, movement of the said guide block 23 is not affected.

Figure 43:
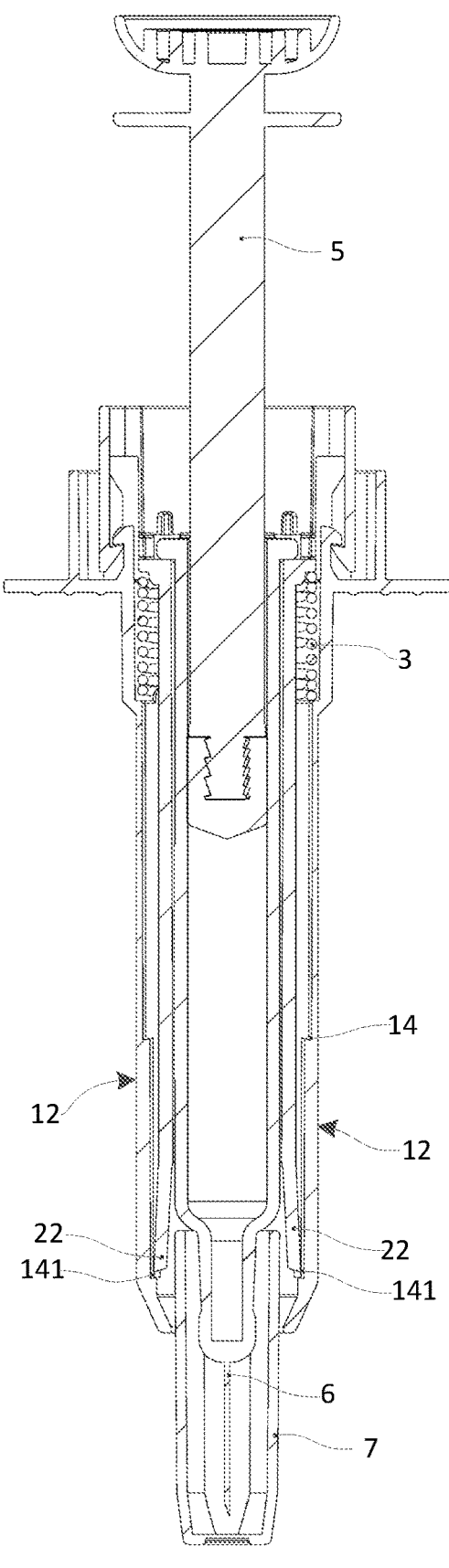
FIG. 43 is section view of assembling structure of the safety syringe without convex structure.

As shown in FIG. 43, after assembling of the syringe protector of the disclosure, the said backstop jaw 22 is arranged inside the said outer sleeve tube body 12, in particular to the said backstop jaw 22 contained in the said inner guide chute 141 to protect the locking status of the device, the said backstop jaw 22 shall be far enough from the central axis, which will not affect the needle sleeve 7 and removal of the needle sleeve. After the protector activation is finished, the said backstop jaw 22 slides within the said inner guide chute 141, and reach the said inner stop orifice 14. Affected by the elasticity, the said backstop jaw 22 further flicks to finish the backstop function and prevent the inner installation sleeve 2 from retracting back to the said outer protection sleeve 1 and exposing the needle 6. After the activation is finished, apply an external stress on the said outer protection sleeve 1 and the said inner installation sleeve 2, try to re-install the inner installation sleeve 2 into the said outer protection sleeve 1, and the said backstop jaw 22 is clipped in the said backstop orifice 14 to prevent retracing.

The syringe protector of the disclosure improves local structure to obtain an outer wall surface of the outer sleeve cylinder body 12 of the complete circle structure for sticking labels, or etching pictures and texts.

The syringe protector of the disclosure, when used as safety syringe, namely the disposal syringe is installed in the said inner installation sleeve 2, and the piston rod 5 is used for medicine injection and activating the syringe protector of the disclosure.

The above discloses and describes basic principle, main characteristics, and advantages of the disclosure. Technicians in the industry shall know that, the disclosure is not restricted by the above embodiment, the above embodiments and description in the specifications only describe the principle of the disclosure, changes and improvements of the disclosure are included under the preconditions of following spirits and scopes of the disclosure, and these changes and improvements fall within the scope of the disclosure. The scope of protection requested by the disclosure is determined by the attached claims and its equivalents.

The invention claimed is:

1. A syringe protector, it is comprised of an outer protection sleeve, an inner installation sleeve, and a spring;
   the outer wall sleeve of the said inner installation sleeve is installed with the said spring, which is compressed and loaded into the said outer protection sleeve, and the syringe protector is formed;

the said outer protection sleeve is comprised of an outer sleeve pipe orifice, an outer sleeve tube body, a guide chute, an inner stop orifice, a spring installation seat, and c;
   the said outer sleeve pipe orifice is arranged at the bottom of the said outer sleeve tube body;
   the wall surface of the said outer sleeve tube body is arranged with the said guide chute;
   the middle of the inner wall of the said outer sleeve tube body is arranged with an inner stop orifice;
   a spring installation seat is arranged on the top of the said outer sleeve tube body, the bottom diameter of the said spring installation seat is higher than the inner diameter of the said outer sleeve tube body, and the said spring is installed in the spring installation seat;
   the inner locking jack catch is arranged above the said spring installation seat, and the number of the said inner locking jack catch is minimum 2 pieces and above along the circumference of the said spring installation seat;
   the said inner installation sleeve is comprised of an inner sleeve tube body, a backstop jaw, a guide block, an outer locking jack catch, a jack catch frame, a releasing slope, a syringe cam fixing jaw, and syringe cam fixing groove;
   the said inner sleeve tube body is installed at the said outer sleeve tube body, which is used to contain the syringe;
   the bottom of the said inner sleeve tube body is arranged with the said backstop jaw, which inclines outwards; under natural status before assembling, the concentric circle diameter at the bottom of the said backstop jaw is larger than the inner diameter of the said outer sleeve tube body;
   a guide block is arranged on the said inner sleeve tube, the said guide block is located at the lower portion of the said inner sleeve tube body and protrudes over the outer wall surface of the inner sleeve tube body; the said guide block is fastened into the said guide chute;
   the top of the said inner sleeve tube body is arranged with the protector locking mechanism, the protector releasing mechanism, and the syringe fixing mechanism;
   the locking mechanism of the said protector is comprised of the outer locking jack catch, which is fastened with the said inner locking jack catch to lock the syringe protector; a suspension arm of the outer locking jack catch is fixed on the said jack catch frame;
   the said releasing mechanism of the protector is comprised of the releasing slope, the said releasing slope is located inside the suspension arm above the said outer locking jack body and below the said jack catch body;
   the said syringe fixing mechanism is comprised of the syringe cam fixing jaw and a syringe cam fixing groove, the said syringe cam fixing groove is arranged at the top of the said inner sleeve tube body, multiple syringe cam fixing jaws are located above the said syringe cam fixing groove, and the guide slope is installed at the said syringe cam fixing jaws;
   the said outer protection sleeve is installed with a locking protection piece, which is arranged outside the said inner locking jack catch; and
   an insertion space for the said outer locking jack catch is reserved between the said inner locking jack catch and the said locking protection piece.

2. The syringe protector as described in claim 1, wherein the said outer protection sleeve is installed with a handle rib, the number of which is 2 pieces, which are arranged on the outer wall of the said spring installation seat or the said outer sleeve tube symmetrically.

3. The syringe protector as described in claim 2, wherein the bottom of the said handle rib is installed with multiple anti-stripping bars.

4. The syringe protector as described in claim 1, wherein an opening of the said outer sleeve pipe orifice inclines inwards and shapes an internal cone.

5. The syringe protector as described in claim 1, wherein the number of the said guide chute is 2 pieces and above and is set on the wall surface of the said outer protection sleeve; and the number of the said guide block is 2 pieces and above, which is arranged on the wall surface of the said inner sleeve tube body.

6. The syringe protector as described in claim 1, wherein inner side at the bottom of the said installation seat is arranged with multiple spring limit protrusions, and the said multiple spring limit clip protrusions are arranged at the top of the said outer sleeve tube body homogeneously; and the inner diameter of the said spring is clipped into the outside of the limit portions comprised of the said multiple spring limit clip protrusions.

7. The syringe protector as described in claim 1, wherein the bottom of the said inner sleeve tube body is arranged with a needle sleeve backstop piece, which inclines inwards; and the concentric circle diameter where the bottom of the said needle backstop piece is less than the inner diameter of the said inner sleeve tube body.

8. The syringe protector as described in claim 7, wherein the said the needle sleeve backstop piece and the said backstop jaw are minimum 2 pieces; and the said needle sleeve piece and the said backstop jaw are scattered at the bottom of the said inner sleeve tube body homogeneously and alternatively.

9. The syringe protector as described in claim 1, wherein the bottom of the said guide block is communicated with the said inner sleeve tube body through the connecting bar, the upper portion of the said guide block is suspended in air, and the guide block inclines inwards along the said connecting bar.

10. The syringe protector as described in claim 9, wherein a window is located at the said inner sleeve tube body where the said guide block is located, and the direction of the said window is corresponding to the direction of the said guide chute.

11. The syringe protector as described in claim 1, wherein a piston fixing step is arranged at the lower portion of the said releasing slope and is located inside the suspension arm above the said outer locking jack catch; the said piston fixing step is higher than the top of the said syringe cam fixing jaw.

12. The syringe protector as described in claim 1, wherein the said outer protection sleeve and the said inner installation sleeve are installed with the inner locking jack catch and the outer locking jack catch with the left and right limit structures to form a safety snap joint; under natural status, the said outer locking jack catch fastens the said inner locking jack catch inwards; and the body of the said inner locking jack catch contacts the body of the said outer locking jack catch, with left and right limit structures.

13. The syringe protector as described in claim 12, wherein both sides of the said outer locking jack catch are installed with the inner jack catch limit body, and an inner jack catch storage groove is formed between the inner jack catch limit body on both sides;

under locking status, the said inner locking jack catch is located within the said inner jack catch storage groove; and the said inner jack catch limit body limits the said inner locking jack catch at the left and right directions.

14. The syringe protector as described in claim 12, wherein the limit structures at the left and right directions are arranged with the inner jack catch surface fastened with the said outer locking jack catch; both sides of the said inner jack catch are arranged with the outer jack body limit body; and under locking status, the jack catch surface of the said outer locking jack catch is clipped between the outer jack catch limit body on both sides and fastened with the said inner jack catch surface; the said outer jack catch limit body limits the said outer jack catch at the left and right directions.

15. The syringe protector as described in claim 12, wherein the said left and right limit structures are, a groove is made in the middle of the jack catch body of the said outer locking jack catch to form the inner jack catch storage groove, and the inner jack catch limit body is arranged on both sides of the jack catch body of the said outer locking jack catch;

a convex inner jack catch protrusion is arranged at the lower portion of the jack catch body of the said inner locking jack catch; the width of the said inner jack catch matches the width of the said jack catch storage groove; and under locking status, the said inner locking jack catch contacts the said outer locking jack catch, and the said inner jack catch protrusion is clipped into the said inner jack catch storage groove.

16. The syringe protector as described in claim 12, wherein the said left and right limit structure is that, a groove is made in the middle of the said inner locking jack catch to form the outer jack catch storage groove;

the outer jack catch protrusion is located below the middle of the said outer locking jack catch; the width of the said outer jack catch matches the width of the said outer jack storage groove; and under locking status, the said inner locking jack catch contacts the said outer locking jack catch, and said outer jack catch protrusion is clipped into the said outer jack catch storage groove.

17. The syringe protector as described in claim 1, wherein the outer surface of the outer sleeve tube body of the said outer protection sleeve is free of protrusion;

the middle of the inside wall surface of the outer sleeve tube body of the said outer protection sleeve is arranged with a concave inner stop orifice;

the bottom of the said inner installation sleeve is installed with a backstop jaw; and the said backstop flicks after activation at the said inner installation sleeve and the said outer protection sleeve and clipped above the said inner stop orifice.

18. The syringe protector as described in claim 17, wherein the inside wall surface of the outer sleeve tube body of the said outer protection sleeve is arranged with an inner guide chute, and the said inner stop orifice is located at the said inner guide chute.

19. The syringe protector as described in claim 18, wherein the said backstop jaw is locked at the said inner installation sleeve and the said outer protection sleeve, and is stuck in the said inner guide chute.

20. The syringe protector as described in claim 19, the said outer protection sleeve is installed with a guide chute;

the bottom of the said inner installation sleeve is installed with a guide block; and the said guide block is clipped into the said guide chute.

21. The syringe protector as described in claim 1, including a syringe installed at one of the installation sleeve of the syringe protector.

* * * * *